(12) United States Patent
Salvetat et al.

(10) Patent No.: US 12,084,719 B2
(45) Date of Patent: Sep. 10, 2024

(54) RNA EDITING AS BIOMARKERS FOR MOOD DISORDERS TEST

(71) Applicant: ALCEDIAG, Peynier (FR)

(72) Inventors: Nicolas Salvetat, Montpellier (FR); Jean-François Pujol, Saint Mathieu de Tréviers (FR); Dinah Weissmann, Saint Mathieu de Tréviers (FR); Berengere Vire, Les matelles (FR); Siem Van Der Laan, Cazilhac (FR)

(73) Assignee: ALCEDIAG, Peynier (FR)

( * ) Notice: Subject to any disclaimer, the term of this patent is extended or adjusted under 35 U.S.C. 154(b) by 646 days.

(21) Appl. No.: 16/318,790

(22) PCT Filed: Jul. 28, 2017

(86) PCT No.: PCT/EP2017/069250
§ 371 (c)(1),
(2) Date: Jan. 18, 2019

(87) PCT Pub. No.: WO2018/020042
PCT Pub. Date: Feb. 1, 2018

(65) Prior Publication Data
US 2019/0185937 A1 Jun. 20, 2019

(30) Foreign Application Priority Data
Jul. 28, 2016 (EP) .................................... 16181619

(51) Int. Cl.
*C12Q 1/68* (2018.01)
*C12Q 1/6853* (2018.01)
*C12Q 1/6883* (2018.01)

(52) U.S. Cl.
CPC ......... *C12Q 1/6883* (2013.01); *C12Q 1/6853* (2013.01); *C12Q 2600/118* (2013.01); *C12Q 2600/156* (2013.01)

(58) Field of Classification Search
CPC ........................................................ C12Q 1/68
USPC ............................................................. 435/6
See application file for complete search history.

(56) References Cited

U.S. PATENT DOCUMENTS

2015/0284793 A1   10/2015   Offen et al.

FOREIGN PATENT DOCUMENTS

| JP | 2013529465 A | 7/2013 | |
| WO | WO-2011161253 A1 * | 12/2011 | ......... G01N 33/5023 |

OTHER PUBLICATIONS

Nolan et al, Quantification of mRNA using real-time RT-PCR, Nat Protoc. 2006;1(3):1559-82. doi: 10.1038/nprot.2006.236, p. 1565.*
Wray et al (The genetic interpretation of area under the ROC curve in genomic profiling, PLoS Genet. Feb. 26, 2010;6(2):e1000864. doi: 10.1371/journal.pgen.1000864).*

(Continued)

*Primary Examiner* — Aaron A Priest
(74) *Attorney, Agent, or Firm* — Arrigo, Lee, Guttman & Mouta-Bellum LLP; Carla Mouta-Bellum

(57) ABSTRACT

The present invention is drawn to a method for in vitro predicting the risk for a patient to present a pathology or to identify whether a patient is at risk to develop a pathology, such as psychiatric disorder, associated to an alteration of A-to-I editing on PDE8A transcripts, from body fluids such as a blood, urine or saliva sample of said patient. The present invention also relates to kits for the implementation of the method.

8 Claims, 13 Drawing Sheets
Specification includes a Sequence Listing.

(56) References Cited

OTHER PUBLICATIONS

Cattane et al. (Altered Gene Expression in Schizophrenia: Findings from Transcriptional Signatures in Fibroblasts and Blood, PLoS One. 2015; 10(2): e0116686. Published online Feb. 6, 2015).*

Fan et al. (Differential expression of microRNA in peripheral blood mononuclear cells as specific biomarker for major depressive disorder patients, J Psychiatr Res. Dec. 2014;59:45-52. doi: 10.1016/j.jpsychires.2014.08.007. Epub Aug. 24, 2014).*

International Patent Application No. PCT/EP2017/069250: International Search Report and Written Opinion dated Oct. 17, 2017, 14 pages.

Cavarec et al., "In vitro screening for drug-induced depression and/or suicidal adverse effects: A new toxicogenomic assay based on CE-SSCP analysis of HTR2C mRNA editing in SH-SY5Y cells", Neurotoxicity Research, vol. 23, No. 1, Jan. 1, 2013, pp. 49-62.

Orlowski et al., "Altered editing in cyclic nucleotide phosphodiesterase 8A1 gene transcripts of systemic lupus erythematosus T lymphocytes", Immunology, vol. 125, No. 3, Nov. 1, 2008, pp. 408-419.

Lorenz, "Polymerase chain reaction: basic protocol plus troubleshooting and optimization strategies", Journal of visualized experiments (Jove), 63, May 22, 2012, 14 pages.

Ernst, C., et al., "Alternative Splicing, Methylation State, and Expression Profile of Tropomyosin-Related Kinase B in the Frontal Cortex of Suicide Completers", 2009, Arch Gen Psychiatry 66, pp. 22-32.

Bani-Fatemi, A., et al., "Epigenetic studies of suicidal behavior", Neurocase: The Neural Basis of Cognition, Jan. 31, 2014, Neurocase, 2015, vol. 21, No. 2, pp. 134-143.

Kaminsky, Z., et al., "Epigenetic and genetic variation as SKA2 predict suicidal behavior and post-traumatic stress disorder", Citation: Transl Psychiatry (2015) 5, e627, www.nature.com/tp, pp. 1-7.

Weissman, D. et al., "Region-specific alterations of A-to-I RNA editing of serotonin 2c receptor in the cortex of suicides with major depression", Transl Psychiatry (2016) 6, e878, Aug. 30, 2016, pp. 2-9.

Dracheva, S., et al., "Increased serotonin 2C receptor MRNA editing: a possible risk factor for suicide", Molecular Psychiatry (2008) 13, pp. 1001-1010, www.nature.com/mp.

Dracheva, S. et al., "Editing of Serotonin 2C Receptor mRNA in the Prefrontal Cortex Characterizes High-Novelty Locomotor Response Behavioral Trait", Neuropsychopharmacology (2009) 34, pp. 2237-2251.

Simmons, M., et al., "Increased cortical expression of an RNA editing enzyme occurs in major depressive suicide victims", Behavioral, integrative and clinical neuroscience, NeuroReport 2010, vol. 21, No. 15, pp. 993-997.

Wang, P., et al., "Human phosphodiesterase 8A splice variants: cloning, gene organization, and tissue distribution", Elsevier, Gene 280 (2001) pp. 183-194.

Morse, D.P. et al., "RNA hairpins in noncoding regions of human brain and Caenorhabditis elegans MRNA are edited by adenosine deaminases that act on RNA", PNAS, Jun. 11, 2002, vol. 99, No. 12, pp. 7906-7911.

Ge, Y. et al., "Resampling-based multiple testing for microarray data analysis", Jan. 2003, Technical Report #633, pp. 1-41.

Gentleman, R.C. et al., "Bioconductor: open software development for computational biology and bioinformatics", Genome Biology 2004, vol. 5, Issue 10, Article R80, Sep. 15, 2004, http://genomebiology.com/2004/5/10/R80, pp. 1-16.

Kramar, A., et al., "mROC: a computer program for combining tumour markers in predicting disease states", Elsevier, Computer Methods and Programs in Biomedicine 66 (2001), pp. 199-207.

Su, J.Q., et al., "Linear Combinations of Multiple Diagnostic Markers", Journal of the American Statistical Association, 88:424, Dec. 1993, pp. 1350-1355.

Wang, "A note on iterative marginal optimization: a simple algorithm for maximum rank correlation estimation", Elsevier, ScienceDirect, Computational Statistics & Data Analysis 51 (2007), pp. 2803-2812.

Staack, A. et al., "Combined determination of plasma MMP2, MMP9, and TIMP1 improves the non-invasive detection of transitional cell carcinoma of the bladder", BMC Urology 2006, 6:19, BioMed Central, Aug. 10, 2006, pp. 1-12.

Soukas, A. et al., "Leptim-specific patterns of gene expression in white adipose tissue", Genes & Development 14, 2000, pp. 963-980.

Levanon, E.Y. et al., "Systematic identification of abundant A-to-I editing sites in the human transcriptome", 2004, Nat Biotechnol 22, 33 pages.

Porath, H.T. et al., "A genome-wide map of hyper-edited RNA reveals numerous new sites", Nature communications. Aug. 27, 2014, pp. 1-10.

Udina, M. et al., "Interferon-induced Depression in Chronic Hepatitis C: A Systematic Review and Meta-Analysis", J Clin Psychiatry, Aug. 2012, 73(8), abstract only, 2 pages.

Asnin, G.M. et al., "Interferon-Induced Depression in Chronic Hepatitis C: A Review of Its Prevalence, Risk Factors, Biology, and Treatment Approaches", J Clin Gastroenterol, vol. 40, No. 4, Apr. 2006, pp. 322-335.

Asnis, G.M. et al., "IFN-Induced Depression: A role for NSAIDs", Translational Neuroscience, Psychopharmacology Bulletin: Summer 2003, vol. 37, No. 3, 29, 23 pages.

George, C.X. et al., "Human RNA-specific adenosine deaminase ADAR1 transcripts possess alternative exon 1 structures that initiate from different promoters, one constitutively active and the other interferon inducible", Proc. Natl. Acad. Sci, USA, vol. 96, Apr. 1999, pp. 4621-4626.

Borges, G. et al., "Risk factors for twelve-month suicide attempts in the National Comorbidity Survey Replication (NCS-R)", Psychol Med., Dec. 2006, 36(12), pp. 1747-1757.

Brown, G.K. et al., "Risk factors for suicide in psychiatric outpatients: A 20-year prospective study", APA PsycNet, Journal of Consulting and Clinical Psychology 68(3), 2000, Abstract only, 2 pages.

Brown, G.K. et al., "Risk factors for suicide in psychiatric outpatients: A 20-year prospective study", Journal of Consulting and Clinical Psychology, vol. 68, No. 3, 2000, pp. 371-377.

Cedereke, M. et al., "Prediction of repeated parasuicide after 1-12 months", European Psychiatry, 20(2), 2005, 23 pages.

Heyerdahl, F. et al., "Repetition of acute poisoning in Oslo: 1-year prospective study", The British Journal of Psychiatry (2009) 194, pp. 73-79.

* cited by examiner

FIG. 11A-11B-11C-11D
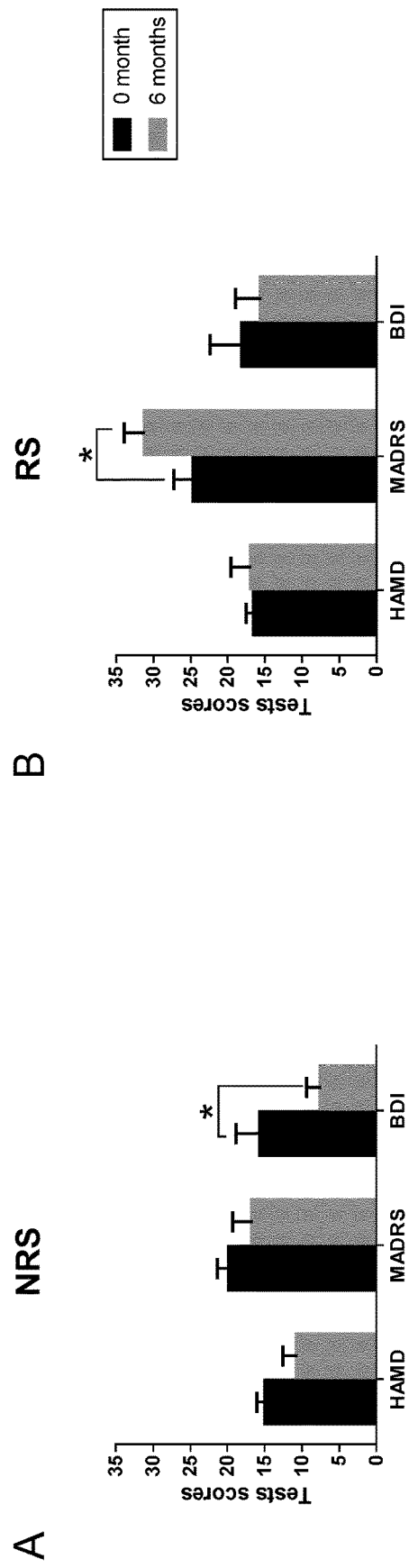
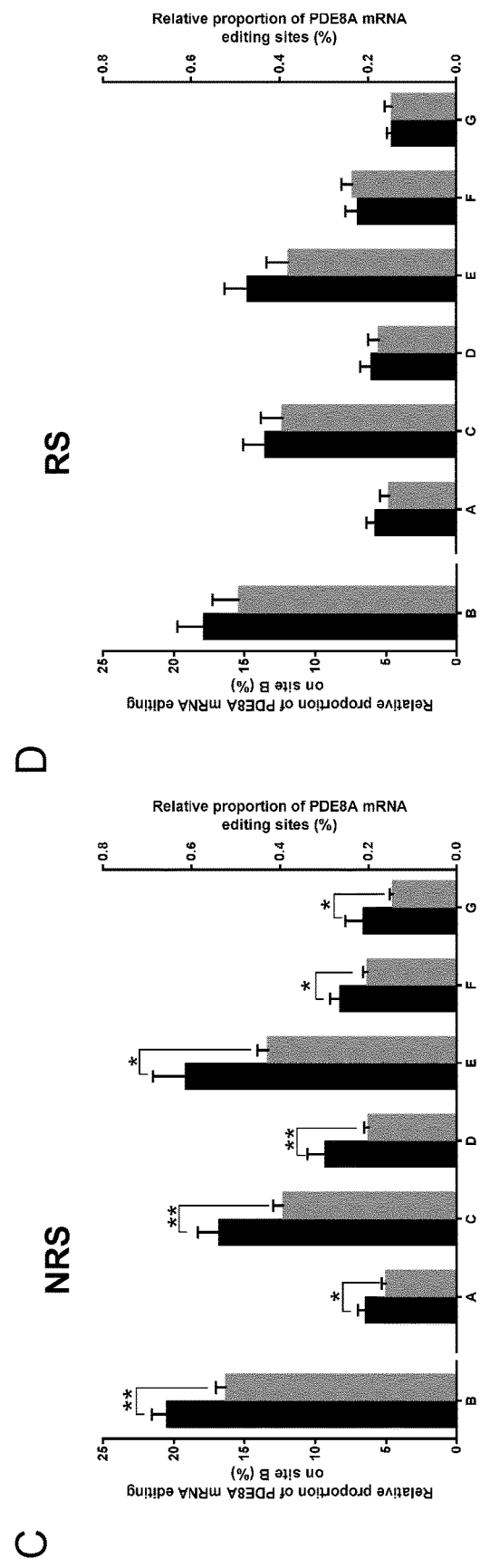

FIG. 12A-12B-12C
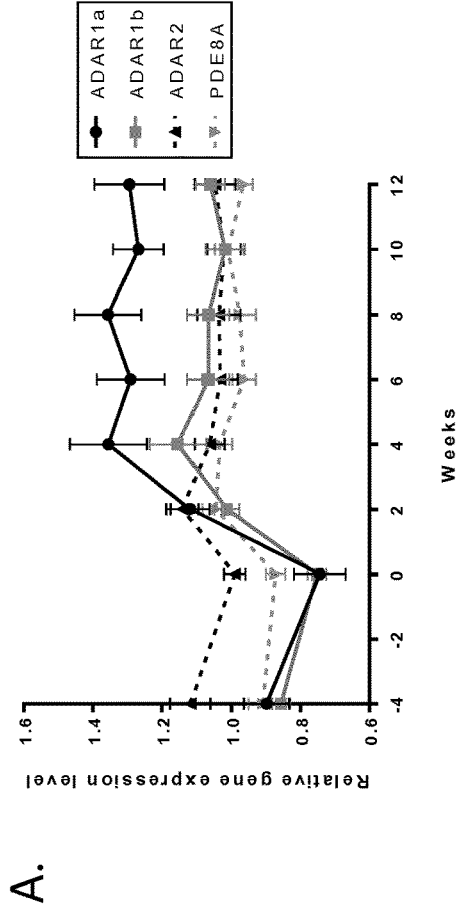
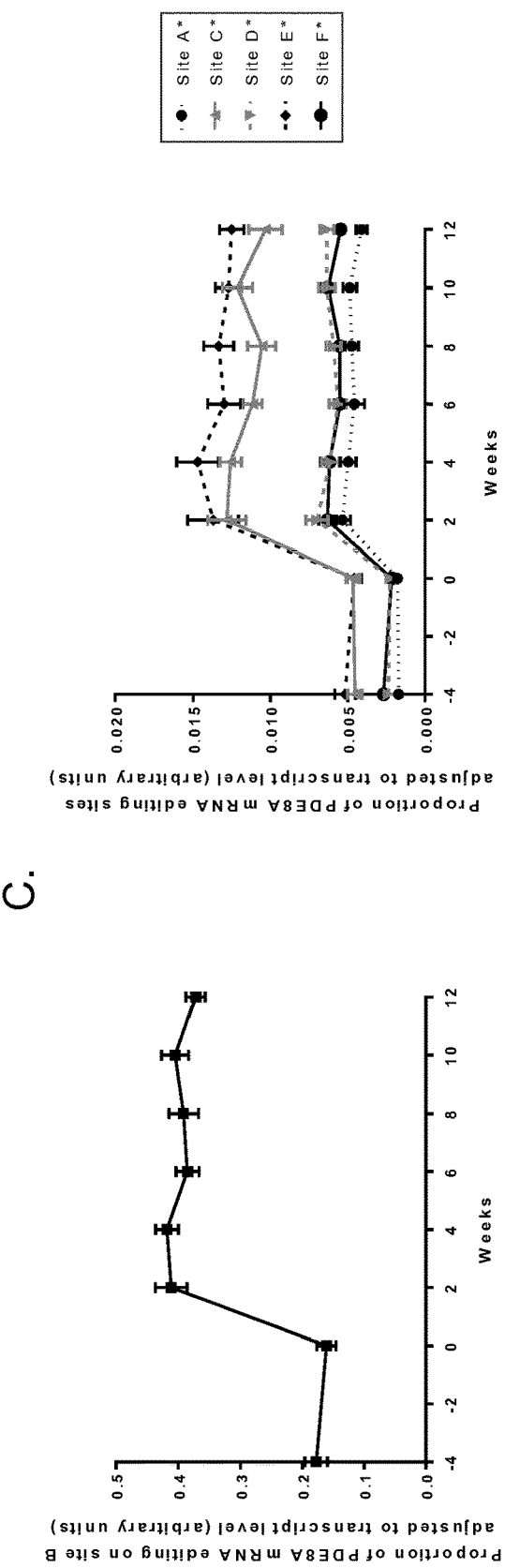

|          | Week 2 | Week 4 | Week 6 | Week 8 | Week 10 | Week 12 |
|----------|--------|--------|--------|--------|---------|---------|
| Patient 1 |        |        |        |        |         |         |
| Patient 2 | False negative | | | | | |
| Patient 3 | False negative | | | | | |
| Patient 4 |        |        |        | False positive | | |
| Patient 5 |        |        |        |        |         |         |
| Patient 6 |        |        |        |        |         |         |
| Patient 7 |        | False positive | | | | |
| Patient 8 |        |        |        | False positive | | |
| Patient 9 |        |        |        |        | False negative | |
| Patient 10 |       |        |        |        |         |         |

Patients with psychiatric event: Patient 1–Patient 3
Patients without psychiatric event: Patient 4–Patient 10

FIG. 14 ary genomic research have unveiled that multiple factors

```
                       SEQUENCE LISTING

<160> NUMBER OF SEQ ID NOS: 6

<210> SEQ ID NO 1
   <211> LENGTH: 225
   <212> TYPE: DNA
   <213> ORGANISM: artificial
   <220> FEATURE:
   <223> OTHER INFORMATION: Sequence of interest located within intron 9 of
         the human PDE8A gene

<400> SEQUENCE: 1
atgcaagttg tggacatgga ggacaaccca cttatttctg cctagggaac cctgtttagt     60
ccttggtggc tttggactac aagcctcgtc ctgtgggctg agctccccct cagaactgta    120
ccaaggccca tacctccctt ctactccagt gtgacctaag gactcagctg ggctttctgg    180
ctgttttttg atatagccct tttttggtgc ccattgtttt cagaa                    225

<210> SEQ ID NO 2
   <211> LENGTH: 20
   <212> TYPE: DNA
   <213> ORGANISM: artificial
   <220> FEATURE:
   <223> OTHER INFORMATION: Sequence "Seq1-Forward"

<400> SEQUENCE: 2
acctgtctgc tgaagccttc                                                 20

<210> SEQ ID NO 3
   <211> LENGTH: 21
   <212> TYPE: DNA
   <213> ORGANISM: artificial
   <220> FEATURE:
   <223> OTHER INFORMATION: Sequence "Seq2-Forward"

<400> SEQUENCE: 3
atgcaagttg tggacatgga g                                               21

<210> SEQ ID NO 4
   <211> LENGTH: 20
   <212> TYPE: DNA
   <213> ORGANISM: artificial
   <220> FEATURE:
   <223> OTHER INFORMATION: Sequence "Seq1-Reverse"

<400> SEQUENCE: 4
ccttccagag tccctcagga                                                 20
```

```
<210> SEQ ID NO 5
<211> LENGTH: 20
<212> TYPE: DNA
<213> ORGANISM: artificial
<220> FEATURE:
<223> OTHER INFORMATION: Sequence "Seq2-Reverse"

<400> SEQUENCE: 5
ttctgaaaac aatgggcacc                                              20

<210> SEQ ID NO 6
<211> LENGTH: 21
<212> TYPE: DNA
<213> ORGANISM: artificial
<220> FEATURE:
<223> OTHER INFORMATION: Sequence "Seq3-Reverse"

<400> SEQUENCE: 6
ttctgaaaac aatgggcacc a                                            21
```

RNA EDITING AS BIOMARKERS FOR MOOD DISORDERS TEST The present invention is drawn to a method for in vitro predicting the risk for a patient to present a pathology or to identify whether a patient is at risk to develop a pathology, such as psychiatric disorder, associated to an alteration of A-to-I editing on PDE8A transcripts, from body fluids such as a blood, urine or saliva sample of said patient. The present invention also relates to kits for the implementation of the method.

Suicide and suicidal behaviour are among major public health issues worldwide, as 1 million cases of completed suicides are reported in most Western countries and this is expected to rise up to 1.5 million by 2020. Today, suicide risk prevention using biologic tools is not validated, and clinical evaluation doesn't allow a good prediction of the occurrence of suicidal behaviour in a given patient. Furthermore, pharmacological treatments of psychiatric diseases have shown their limited effect on decreasing the rate of attempted and completed suicides. There is a pressing public health need to develop new strategies and promote preventive actions toward those most at risk for suicide. To achieve this goal, suicide prevention strategies require identification of individuals at risk.

Among the many factors involved in determining suicidal behaviour, some recent developments in molecular genetics and genomic research have unveiled that multiple factors may contribute to susceptibility for suicidal behaviour. This susceptibility is likely mediated by an underlying genetic predisposition interacting with environmental and epigenetic factors throughout the lifespan to modify the function of neuronal circuits [1-3]. RNA editing of receptors expressed in synaptic clefts and other associated proteins has been shown to be involved in etiology of different psychiatric disorders and linked to suicidal behaviour [4-7]. Simmons and colleagues have recently reported an increase in the expression of the RNA editing enzyme 1, Adenosine Deaminase Acting on RNA (ADAR1) mRNA in the cerebral cortex of depressive suicide victims [8]. The phospho di-esterase 8A (PDE8A) which is a target of ADARs, is expressed both in brain and blood tissues, and edited by ADARs in humans [9-11]. Alteration in the editing profile of PDE8A pre-mRNA which can by quantitatively evaluated from total RNA extracts of human tissues, including brain but practically more convenient also in blood samples, can be used to monitor the status of a patient. Based on these observations, the objective is to identify body fluids biomarkers to determine disease-specific molecular signatures. Application of this body fluids test will open new possibilities to evaluate primary or secondary risks of severe psychiatric side effects.

To date, no test has been specifically approved by the U.S. Food and Drug Administration (FDA), or by other drug regulatory agencies, as an effective test for predicting the risk for a patient to present or to develop a psychiatric disorder, such as depressive disorder or suicidal behaviour.

There is a great interest in reviewing any test that might demonstrate efficacy to determine the risk of suicidal behaviour or depressive disorder for a patient.

Today, there is no approved biological test to identify such patients.

Thus there is a need to provide with in vitro test, particularly easy to use from for example a blood sample of the patient to be tested, which can determine with high accuracy and with high discriminate power the risk for a patient to present or to develop a psychiatric disorder, such as depressive disorder or suicidal behaviour.

This is the object of the present invention.

In a first aspect, the present invention is directed to an in vitro method for predicting the risk for a patient to present a pathology or to identify whether a patient is at risk to develop a pathology, said pathology being selected from the group consisting of psychiatric disorder or neurological, immunological and degenerative syndromes associated to an alteration of A-to-I editing on PDE8A transcripts, said method comprising the following steps of:

from body fluids sample of said patient containing cells expressing the at least one of the editing enzymes ADAR1a, ADAR1b and ADAR2 and the PDE8A a) determining in a same cellular RNA extract obtained from said blood sample containing cells:
i) the PDE8A mRNA expression level, and
ii)—the level of the PDE8A RNA editing of at least one or a combination of sites which can be edited on the PDE8A gene and, preferably, associated with said pathology), and/or
the level of the expression of at least one or a combination of PDE8A isoforms or the non-edited transcript (Ne) which can be expressed and, preferably, associated with said pathology; and
b) determining the relative proportion of said RNA editing site(s) and/or said PDE8A isoform(s) level to the PDE8A mRNA expression level from the results obtained in step a); and
c) identifying whether said patient presents or is at risk to develop said pathology by:
i) comparing the relative proportion of RNA editing at said site(s) and/or isoform(s) obtained in step b) with the relative proportion of said RNA editing site(s) and/or isoform(s) obtained from control body fluids samples of patients known to exhibit or not, or to be at risk or not to develop, said pathology, and/or
ii) applying an algorithm or statistical model exhibiting a discriminative performance using said edited site(s) and/or isoform(s), or combination thereof, selected in step b), and, using the results or the end value obtained in step c) i) or ii) to determine whether said patient presents or is at risk to develop said pathology.

The threshold value determined for the control sample in step c)i) or the algorithm used in step c)ii) can be obtained for example by a method comprising the steps of:
a)—selecting a collection of patients composed of a ratio of patients annotated with or without a risk to develop a psychiatric disorder or to identify the patient as presenting a psychiatric disorder,
selecting one or several PDE8A RNA editing sites and/or isoform(s), or a combination thereof;
b) analysing the target PDE8A RNA editing sites and/or isoform(s) in order to obtain the proportion of RNA editing level of said target site(s) or isoforms and for each of the patients of said collection,
c)—i) by an univariate analysis statistical method, evaluating for each RNA edited site and/or isoform, its threshold value and/or its accuracy and power to discriminate the risk to develop the said pathology, such as psychiatric disorder, or to identify the patient as presenting said pathology, and/or
ii) by a multivariate analysis statistical method, evaluating for each combination of RNA edited sites and/or isoforms, its accuracy and its power to discriminate the risk to develop said pathology, particularly a psychiatric disorder, or to identify the patient as presenting said pathology, and
iii) selecting the editing site and/or isoform or combination thereof exhibiting an acceptable discriminative performance; and e) building an algorithm using said selected combination of editing sites and/or isoforms, and use said algorithm thus obtained for predicting for a given patient the risk to develop said pathology, particularly a psychiatric disorder, or to identify said patient as presenting said pathology.

In a preferred embodiment, the algorithm which can be used in the method according to the invention, is carried out by a multivariate method including:

mROC program, particularly to identify the linear combination, which maximizes the AUC (Area Under the Curve) ROC and wherein the equation for the respective combination is provided and can be used as a new virtual marker Z, as follows:

$$Z = a_1 \cdot (\text{Biomarker 1}) + a_2 \cdot (\text{Biomarker 2}) + \ldots a_i \cdot (\text{Biomarker } i) + \ldots a_n \cdot (\text{Biomarker } n)$$

where $a_i$ are calculated coefficients and (Biomarker i) are the relative proportion of individual level of RNA editing site or of isoform's target; and/or a logistic regression model applied for univariate and multivariate analysis to estimate the relative risk of patient at different level of RNA editing site or isoforms values; and/or a CART (Classification And Regression Trees) approach applied to assess RNA editing site(s) and/or isoforms combinations; and/or a Random Forest (RF) approach applied to assess the RNA editing site(s) and/or isoforms combinations, particularly to rank the importance of the RNA editing site(s) and/or isoform(s), and to combine the best RNA editing site(s) and/or isoform(s) to classify the "relative risk", and/or optionally a multivariate analysis applied to assess the RNA editing site(s) and/or isoforms combinations for the "relative risk", said multivariate analysis being selecting for example from the group consisting of as Support Vector Machine (SVM) approach;
Artificial Neural Network (ANN) approach;
Bayesian network approach;
WKNN (weighted k-nearest neighbours) approach;
Partial Least Square—Discriminant Analysis (PLS-DA);
Linear and Quadratic Discriminant Analysis (LDA/QDA), and
Any other mathematical method that combines biomarkers In a preferred embodiment, the body fluid sample is selected from the group of blood, urine and saliva sample, blood sample being the most preferred.

In a preferred embodiment, said pathology is a psychiatric disorder.

In another preferred embodiment, said pathology is selected from the group consisting of mental disorders, bipolar disorder, depressive disorders, schizophrenia, panic disorder, social anxiety, post-traumatic stress disorder (PTSD), substance dependence/abuse, abnormal feeding behaviour, preferably anorexia or obesity, obsessive compulsive disorder (OCD), early Alzheimer's disease, or Parkinson's disease.

In a more preferred embodiment, said pathology is a depressive disorder and more particularly suicidal behaviour.

In a more preferred embodiment of the method of the present invention, said method is for predicting the risk for a patient to attempt suicide, and wherein in step c)(i), the control body fluids samples is obtained from affecting controls group of patients.

In also more preferred embodiment of the method of the present invention, said method is a method to identify whether a patient exhibits a depression disorder, and wherein in step c)(i), the control body fluids samples is obtained from healthy group of patients.

In a particular embodiment, in the method according to the present invention, said patient is selected from patients already identified to present a psychiatric disorder which can be associated to a risk to develop a suicidal behaviour, particularly depressive disorder with or without history of suicide attempts and wherein in step c), it is identified whether said patient presents or is at risk to develop a suicidal behaviour.

In another embodiment, the method of the present invention allows to monitor and/or stratify patients between responder and non-responders to treatment.

Many disorders such as psychiatric disorders are known to sometimes be associated with suicidality. In some embodiments, the patient is suffering from mental disorders, bipolar disorder, schizophrenia, panic disorder, social anxiety, post-traumatic stress disorder (PTSD), substance dependence/abuse, eating disorder (abnormal feeding behaviour (like anorexia, obesity), obsessive compulsive disorder (OCD), early Alzheimer's disease, or Parkinson's disease.

In another embodiment, said patient can be a patient identified as not presenting a psychiatric disorder and treated for a non-psychiatric disorder, particularly treated against hepatitis.

Another aspect of the invention concerns the method of the present invention which further comprises:

in step a) the determination of the quantitative expression of the editing enzymes ADAR1a, and/or ADAR1b and/or ADAR2 in the same cellular extract; and in step c), it is identified whether said patient presents or is at risk to develop said pathology by:

i) further comparing the quantitative expression of the editing enzymes ADAR1a and/or ADAR1b and/or ADAR2 obtained in step b) with those obtained for normal patients and, optionally for patients exhibiting pathologies associated to an alteration of A-to-I editing on PDE8A transcripts, and/or ii) applying an algorithm or statistical model exhibiting a discriminative performance using said edited site(s) and/or isoform(s), and ADARs expression, or combination thereof, selected in step a) and b).

In a preferred embodiment of the method of the present invention, said blood sample contains PBMC (Peripheral Blood Mononuclear Cells);

Preferably, in the method according to the present invention, in step a), the determination of the PDE8A RNA editing of a one site is carried for at least one site selected from the edited sites listed in Table III, more preferably for a several sites comprising at least one site O to ZZ of the Table III.

Preferably, in the method according to the present invention, in step a), the determination of the PDE8A RNA editing of a one site or of several sites is carried for at least site (s) selected from the group consisted of the sites A, B, C, D, E, F, G, Z, and ZZ.

More preferably, in the method according to the present invention, in step a), the determination of the PDE8A RNA editing of a one site or of several sites is carried for at least the site B.

Preferably, in the method according to the present invention, in step a), it is determined the relative proportion of PDE8A RNA isoform level comprising only said one site edited or a combination of some of said several sites edited to the PDE8A mRNA expression level.

Preferably, in the method according to the present invention, in step a), it is determined the relative proportion of PDE8A RNA isoform(s) selected from the group of isoforms B, BC, D, E, Ne (Non-edited), BE, G, BG, BF, A, Z, C, F, BZ and BD.

More preferably, in the method according to the present invention, in step a), it is determined at least the relative proportion of PDE8A RNA isoform B.

In a preferred embodiment, in the method of the present invention, said algorithm or statistical method in step c) includes:

mROC program, particularly to identify the linear combination, which maximizes the AUC (Area Under the Curve) ROC and wherein the equation for the respective combination is provided and can be used as a new virtual marker Z, as follows:

$$Z = a_1 \cdot (\text{Biomarker } 1) + a_2 \cdot (\text{Biomarker } 2) + \ldots a_i \cdot (\text{Biomarker } i) + \ldots a_n \cdot (\text{Biomarker } n)$$

where $a_1$ are calculated coefficients and (biomarker i) are the relative proportion of individual PDE8A RNA editing level of one site or one isoform target or the level of ADAR1a, 1b or ADAR2 expression; and/or a logistic regression model applied for univariate and multivariate analysis to estimate the relative risk for a given patient at different edited site (s) and/or isoform(s) and/or ADARs values.

Or any other mathematical method that combines biomarkers.

Preferably, in the method according to the present invention, in step c), said algorithm is selected from the group consisted of the mROC combinations as listed in Table VI.

Preferably, in the method according to the present invention, in step a) and b), the determination of the PDE8A mRNA expression level by qPCR and/or the level of the RNA editing of a one site is carried out by the NGS (Next Generation Sequencing) method.

In a preferred embodiment, the determination of the PDE8A mRNA expression level by qPCR and/or the level of the RNA editing at a given site is carried out using a set of a forward and reverse primers selected from the group of:

Seq1-Forward (SEQ ID No. 2) or Seq2-Forward (SEQ ID No. 3) for the forward primer;

Seq1-Reverse (SEQ ID No. 4), Seq2-Reverse (SEQ ID No. 5) or Seq3-Reverse (SEQ ID No. 6) for the reverse primer, and A set of a forward and reverse primer meeting the following selection criteria:
i) the oligo's should be between 18-27 nucleotides long,
ii) with preferentially a melting temperature surrounding 60° C. (57-63° C.),
iii) an optimal GC content surrounding 50% (±5%),
iiii) a maximum allowable length of 5 mononucleotide repeat, and
vi) specifically amplify the region of interest depicted in FIG. 1.

In a more preferred embodiment, the following set of primers Seq2-Forward and Seq-3 Reverse is used in the method of the present invention to determine the level of RNA editing of PDE8A on one site.

In another aspect, the invention concerns a kit for determining whether a patient is at risk to present a pathology or to identify whether a patient is at risk to develop a pathology selected from the group consisting of psychiatric disorder or neurological, immunological and degenerative syndromes associated to an alteration of A-to-I editing on PDE8A transcripts, said kit comprising:

1) instructions to apply the method according to the present invention, in order to obtain the end value the analysis of which determining said risk to induce pathology, said instructions comprising optionally a ROC curve; and 2) a set of a forward and reverse primers selected from the group of:

Seq1-Forward (SEQ ID No. 2) or Seq2-Forward (SEQ ID No. 3) for the forward primer;

Seq1-Reverse (SEQ ID No. 4), Seq2-Reverse (SEQ ID No. 5) or Seq3-Reverse (SEQ ID No. 6) for the reverse primer, and A set of a forward and reverse primer meeting the following selection criteria:
i) the oligo's should be between 18-27 nucleotides long,
ii) with preferentially a melting temperature surrounding 60° C. (57-63° C.),
iii) an optimal GC content surrounding 50% (±5%),
iiii) a maximum allowable length of 5 mononucleotide repeat, and
vi) specifically amplify the region of interest depicted in FIG. 1.

In a more preferred embodiment, the kit comprises the following set of primers Seq2-Forward (SEQ ID No. 3) and Seq-3 Reverse (SEQ ID No. 6).

The following examples and the figures and the legends hereinafter have been chosen to provide those skilled in the art with a complete description in order to be able to implement and use the present invention These examples are not intended to limit the scope of what the inventor considers to be its invention, nor are they intended to show that only the experiments hereinafter were carried out.

Other characteristics and advantages of the invention will emerge in the remainder of the description with the Examples and Figures, for which the legends are given hereinbelow.

BRIEF DESCRIPTION OF THE DRAWINGS

FIGS. 11A-11D: Clinical evaluations of the non-repeat suicidal attempters (NRSA) group and the repeat suicidal attempters (RSA) in a follow up study over a period of 6 months. Hamilton (HAMD), MADRS (Montgomery-Asberg Depression Rating Scale) and BDI (Beck Depression Inventory) scores are given for both groups at initial intake at 0 month and at 6 months (A-B). Corresponding RNA editing quantification on all the sites of the PDE8A genes (C-D). Data represent the mean of 5 replicates and error bars represent the standard error of the mean. The p-values were calculated using Wilcoxon test.

FIGS. 12A-12C: (A) Longitudinal analysis of ADAR1a, ADAR1b, ADAR2 and PDE8A gene expression of all HCV patients (n=10) during 16 weeks. (B) Longitudinal analysis of RNA editing on site B of the PDE8A gene of all HCV patients adjusted to the relative PDE8A transcript level (n=10). (C) Longitudinal analysis of RNA editing on the other identified sites of the PDE8A gene of all HCV patients adjusted to the relative PDE8A transcript level (n=10). The mean values are displayed ±SEM (n=10).

FIG. 14: A specific combination of biomarkers was applied to all data points obtained over the course of IFN treatment.

EXAMPLE 1: MATERIALS AND METHODS

1) Human Participants

Figure 1:
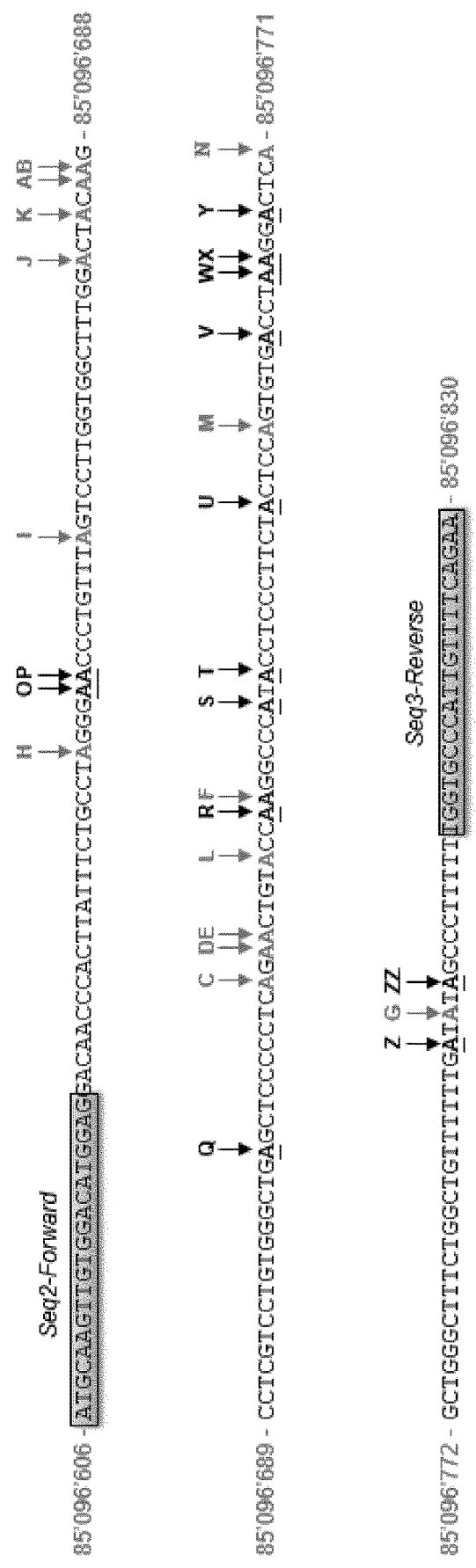
FIG. 1:
Sequence of interest located within intron 9 of the human PDE8A gene. An internal sequence (225 bp) of intron 9 (base positions 85,096,606 to 85,096,830, SEQ ID No. 1) is shown. This sequence is amplified using the primer combination Seq2 Forward and Seq3 Reverse. Previously described editing sites by Orlowski and collaborators (A to H) [10] and by Weissmann et al. (Patent WO 2011/161253) are depicted in grey bold capital letters above the sequence. New editing sites O to ZZ are depicted in black bold underlined capital letters above the sequence.
Figure 2:
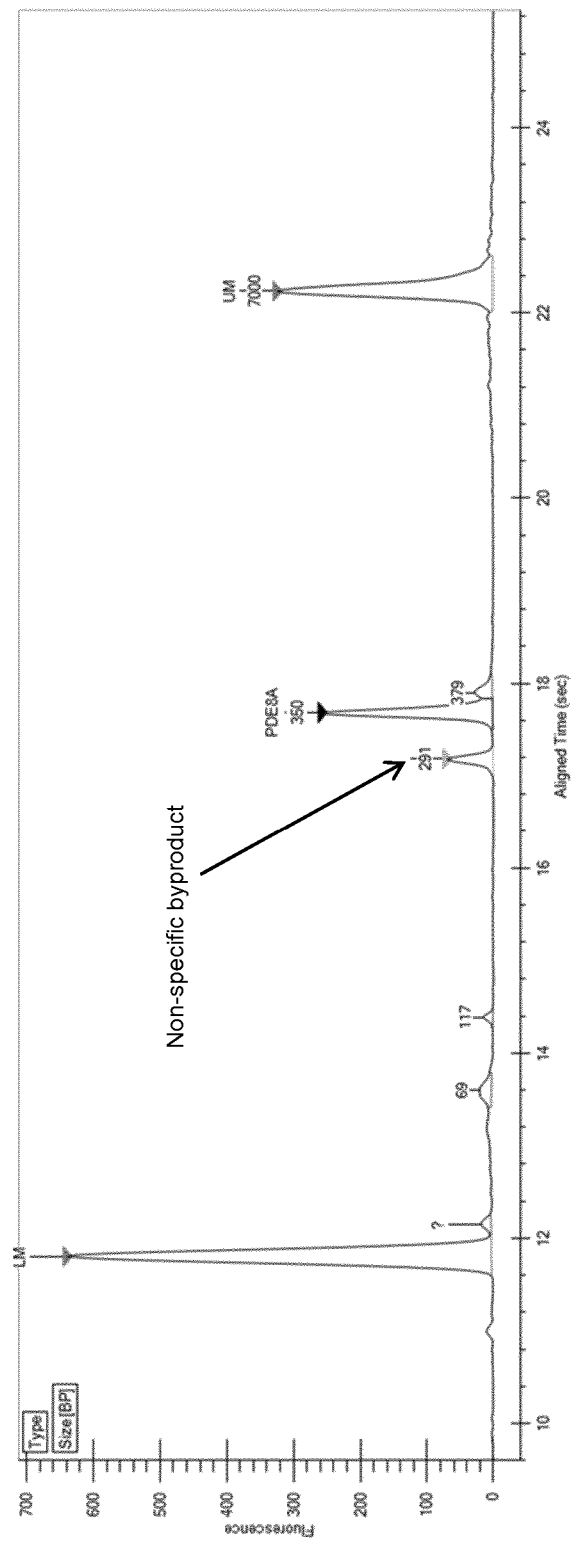
FIG. 2:
Typical electrophoregram displaying nonspecific byproducts obtained with amplification using various primer pairs. The primer pair comprising of Seq2-Forward and Seq3-Reverse that did not produce detectable nonspecific products was used for amplification of the target region of PDE8A and ultra-deep sequencing.

Data from two different cohorts are presented: one cohort including depressed patients with or without history of suicide attempts (called the Suicide attempters study and follow-up) and one longitudinal study that analyses patients infected with hepatitis C virus and that were treated with Interferon α (called the Interferon study). Written informed consent was obtained from all subjects after a detailed discussion on the study aims and requirements. All subjects were able to understand informed consent detailing the research goals and procedure. The study was approved by the local Institutional Review Board, according to the approval requirements and good clinical practice.

2) Suicide Attempters Study and Suicide Attempters Follow-Up Study 2.1 Suicide Attempters Study The study enrolled 38 depressed patients consulting at the Department of Psychiatric Emergency or Post-Emergency of the CHU of Montpellier, France (n=17) or at the Psychiatric Residential Treatment center in Oviedo, Spain (n=21). The psychiatric diagnoses were established by a structured clinical interview. Psychiatric diagnostics were determined according to the Diagnostic and Statistical manual of Mental disorders IV (DSM-IV). The sample included 20 suicide attempters (SA) (52.63%) and 18 suicide non-attempters (affective controls, AC) (47.37%) (see Table I(A)).

Subjects were ethnically homogenous; all were Caucasian, coming from the west of Europe. The demographic data on age and gender were recorded, as well as patient psychiatric diagnosis, alcohol or substance consumption and the suicide attempt number.

TABLE I(A)

Characteristics of patients included in the study. Two groups were included for comparison. The first group termed affective controls (AC) included depressed patients without history of suicide attempts. The second group termed suicide attempters (SA) included depressed patients with history of suicide attempts.

|  | Total sample n (%) | Affective controls n (%) | Suicide attempters n (%) |
|---|---|---|---|
| Number | 38 | 18 (47.37%) | 20 (52.63%) |
| Age (min-max) | 20-77 | 37-77 | 20-75 |
| Mean age (±SD) | 50.16 (±13.5) | 58 (±8.49) | 43.1 (±13.4) |
| Median age | 52.5 | 59 | 45 |

TABLE I(A)-continued

Characteristics of patients included in the study. Two groups were included for comparison. The first group termed affective controls (AC) included depressed patients without history of suicide attempts. The second group termed suicide attempters (SA) included depressed patients with history of suicide attempts.

|  | Total sample n (%) | Affective controls n (%) | Suicide attempters n (%) |
|---|---|---|---|
| Gender |  |  |  |
| Male | 9 (23.68%) | 6 (33.33%) | 3 (15%) |
| Female | 29 (76.32%) | 12 (66.66%) | 17 (85%) |

2.2 Suicide Attempters Follow-Up Study

This follow-up study enrolled 28 depressed suicide attempter's patients consulting at the Department of Psychiatric Emergency or Post-Emergency of the CHU of Montpellier, France. These patients were follow-up over a 6-month period (see Table I(B). During follow-up, 8 patients out of 28 (28.6%) have committed one or several new suicide attempts ("repeat suicide attempters", RSA) while 20 patients (71.4%) did not commit new suicide attempts ("non-repeat suicide attempters", NRSA). Psychiatric assessments of patients were realized as previously mentioned for the suicide attempters study. Depression severity at baseline and follow-up evaluation was assessed using 3 scales: Hamilton Depression scales (HAMD), Montgomery and Asberg Depression rating scale (MADRS) and Beck depression Inventory (BDI) scale.

TABLE I(B)

Characteristics of the 28 patients included in the suicide attempters follow-up study.

|  | Total sample n (%) | NRSA n (%) | RSA n (%) |
|---|---|---|---|
| Number | 28 | 20 (71.4%) | 8 (28.6%) |
| Age (min-max) | 18.9-60.8 | 21.4-60.8 | 18.9-48.4 |
| Mean age (±SD) | 41.8 (±11.9) | 44.3 (±11.4) | 35.8 (±11.6) |
| Median age | 44.2 | 47.03 | 38.5 |
| Gender |  |  |  |
| Male | 7 (25%) | 5 (25%) | 2 (25%) |
| Female | 21 (75%) | 15 (75%) | 6 (75%) |

3) Interferon Study

Figure 8:
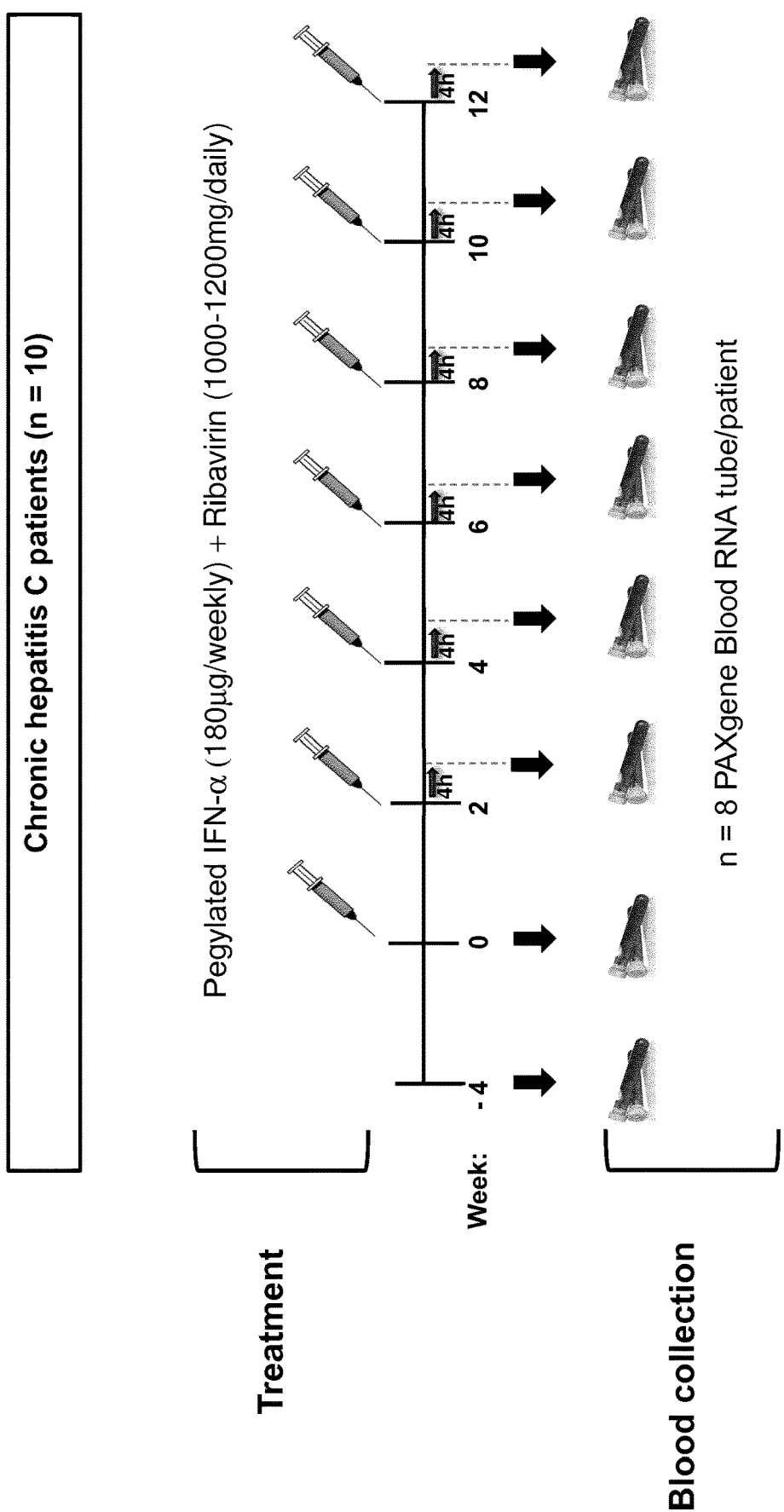
FIG. 8: Longitudinal study of hepatitis C virus (HCV) treated patients with IFN-α and ribavirin. Ten HCV-infected patients were collected on PAXgene Blood RNA tubes 4 weeks before antiviral therapy (−4) and every two weeks after start of treatment (week 0, 2, 4, 6, 8, 10 and 12). The therapy included weekly pegylated IFN-α subcutaneous injections (180 μg) and daily ribavirin tablets (1000-1200 mg).

The study enrolled 10 patients from 3 different departments in CHU (Centre Hospitalier Universitaire) of Marseille, Nancy and Strasbourg (France). Patients infected with hepatitis C virus (HCV), which did not meet any criteria for psychiatric disorders, were enrolled prior to onset of antiviral treatment and followed for up to 12 weeks after onset of antiviral therapy. An initial blood sample was obtained 4 weeks prior treatment (−4). At start of the treatment blood was collected in PAXgene tubes every two weeks for up to 12 weeks (FIG. 8).

4) Blood Retrieval and RNA Extraction and Qualification

A volume of 2.5 ml of whole blood sample from each patient was retrieved in PAXgene blood RNA tubes and stored at −20° C. for a couple of months and then transferred to −80° C. PAXgene™ Blood RNA tubes (PreAnalytix) contain a reagent that protects RNA molecules from degradation by RNAses and ex vivo changes in gene expression. Samples were distributed randomly in the different sets of extractions. Total RNA from the 2.5 ml of whole blood was extracted using the PAXgene™ Blood RNA kit (ref 28704, PreAnalytix). Extracted RNA was isolated using a Qiagen QIAcube system, following the manufacturer's protocol for PAXgene Blood RNA part 1, automated protocol. During sample preparation and RNA extraction, standard precautions were taken to avoid RNA degradation by RNAses. Total RNA concentrations were determined with a Qubit Fluorometer (Invitrogen) and the Quant-IT RNA BR assay (Invitrogen).

5) NGS Library Preparation

For NGS library preparation a 2-step PCR method was employed in order to selectively sequence the region of interest within intron 9 of the PDE8A gene. As shown in FIG. 1, apart from the previously described editing sites, new editing sites in the region of interest have been identified. Validated PCR primers (Seq2 Forward and Seq 3 Reverse) were used to amplify the region of interest by PCR (Table II and FIG. 1).

TABLE II

| Primer name (SEQ ID No.) | Primer Sequence | Length |
|---|---|---|
| Seq1-Forward (SEQ ID No. 2) | ACCTGTCTGCTGAAGCCTTC | 20 |
| Seq2-Forward (SEQ ID No. 3) | ATGCAAGTTGTGGACATGGAG | 21 |
| Seq1-Reverse (SEQ ID No. 4) | CCTTCCAGAGTCCCTCAGGA | 20 |
| Seq2-Reverse (SEQ ID No. 5) | TTCTGAAAACAATGGGCACC | 20 |
| Seq3-Reverse (SEQ ID No. 6) | TTCTGAAAACAATGGGCACCA | 21 |

Sequences of the primers used to measure PDE8A mRNA editing by a Next Generation Sequencing (NGS)-based method. Using a 2-step PCR library preparation protocol a sequencing library containing multiple samples was generated. The library was sequenced on a Next Generation Sequencing system such as the MiSeq platform (Illumina).

For PCR amplification the Q5 Hot Start High Fidelity enzyme (New England Biolabs) was used according to manufacturer guidelines (ref#M0494S). The PCR reaction was performed on a Peqstar 96× thermocycler using optimized PCR protocol. Post PCR, all samples were analysed by LabChipGx (Perkin Elmer) and both quantity and quality of the PCR product was assessed. Purity of the amplicon was determined and quantification was performed using fluorescent based Qubit method. After quality control, the 96 PCR reactions (microplate) were purified using magnetic beads (High Prep PCR MAGbio system from Mokascience). Post purification DNA was quantified using Qubit system and purification yield was calculated. Next, samples were individually indexed by PCR amplification using Q5 Hot start High fidelity PCR enzyme (New England Biolabs) and the Illumina 96 Indexes kit (Nextera XT index kit; Illumina). Post PCR, samples were pooled into a library and purified using Magbio PCR cleanup system. The library was denatured and loaded onto a sequencing cartridge according to Illumina's guidelines for sequencing FASTQ only on a MiSeq platform. A commercial total RNA pool from human blood peripheral leukocytes (Clontech, ref#636592) was incorporated into the libraries to determine variability between different sequencing flow cells during the course of the experiment. NGS libraries were sequenced at standard concentrations and spiked in to introduce library diversity using PhiX Control V3 (Illumina). Experiments were performed five times independently.

6) Bioinformatics Analysis of Sequencing Data

The sequencing data was downloaded from the Miseq sequencer (Illumina) as fastq file. To evaluate sequencing quality, an initial quality of each raw fastq file was performed using FastQC software (version 0.11.3). A pretreatment step was performed consisting of removing adapter sequences and filtering of the sequences according to their size and quality score (all short reads (<50 nts) and reads with average QC<30 were removed). Next, to facilitate and improve the quality of alignment of the sequences flexible read trimming and filtering tools for Illumina NGS data was used (fastx toolkit v0.0.14 and prinseq version 0.20.4). After pre-processing steps were performed an additional quality control of each cleaned fastq file was carried out prior further sequence processing.

Alignment of the processed reads was performed using bowtie2 (version 2.2.5) with end-to-end sensitive mode. The alignment was done to the latest annotation of the human genome sequence (GRCh38) and reads multiple alignment regions, reads with poor alignment quality (Q<40) or reads containing insertion/deletion (INDEL) were taken out of the further analysis. Filtering of file alignment was carried out with SAMtools software (version 1.3.1) that provide various utilities for manipulating alignments in the SAM format, including sorting, merging, indexing and generating alignments in a per-position format.

Next, SAMtools mpileup was used to pileup obtained alignment results data from multiple samples simultaneously. An in-house script was run to count the number of different ATGC nucleotides in each genomic location ('base count'). So, for each genomic location, the home-made script computes the percentage of reads that have a 'G' [Number of 'G' reads/(Number of 'G' reads+Number of 'A' reads)*100]. The genomic location 'A' reference with percentage in 'G' reads >0.1 are automatically detected by the script and are considered as 'A-to-I edition site'. The last stage was to compute the percentage of all possible isoforms of PDE8A transcripts. By definition the relative proportion of RNA editing at a given editing 'site' represents the sum of editing modifications measured at this unique genomic coordinate. Oppositely a mRNA isoform is a unique molecule that may or may not contain multiple editing modifications on the same transcript. Example given, PDE8A mRNA isoform BC contains a modification on both site B and site C within the same transcript.

7) Reverse Transcription and Quantitative Real-Time PCR

Reverse transcription was carried out using the Takara kit (PrimeScript RT, Takara, ref#RR037A). The resulting cDNA was combined with TaqMan universal PCR Master Mix (Applied Biosystems, ref#4369016) and with the following specific gene probes: ADAR1a (Hs01020780), ADAR1b (Hs01017596), ADAR2 (Hs00210562), PDE8A (Hs00400174), GAPDH (Hs02758991), β2M (Hs00984230), HPRT1 (Hs02800695), PGK (Hs99999906) and TBP (Hs00427620) (Applied Biosystems, from Life Technologies) in 20 µl final volume. Quantitative PCR were performed in 96-well plates on StepOnePlus real-time PCR instrument (Applied Biosystems) or in 384-well plates on LightCycler 480 real-time PCR instrument (Roche). For the study performed with depressive patients and suicide attempters, quantification of target gene expression in all patients was normalized to GAPDH and β2M expression and changes in target gene expression in each sample were calculated by $2^{-\Delta\Delta Ct}$. For the study performed with chronic hepatitis C virus (HCV) patients, the analysis was performed using a second derivative absolute quantification, normalized by the geometric mean of four housekeeping genes (GAPDH, HPRT1, PGK and TBP).

8. Statistical Analysis of Data

All statistics and figures were computed with the "R/Bioconductor" statistical open source software and GraphPad Prism software (version 7.0) [12,13]. Biomarkers (i.e RNA editing sites and isoforms of PDE8A and mRNA expression of ADARs) values are usually presented as mean±standard error of the mean (SEM). A differential analysis was carried out using the Mann-Whitney test and a p-value below 0.05 was considered as statistically significant. All data distributions are illustrated as medians and barplots or boxplots for each significant biomarker.

The relative proportion of RNA editing, on both sites and isoforms, were analyzed by adjusting to the relative transcript level of the PDE8A gene. The adjusted RNA editing values were calculated as following:

Adjusted editing value*=(RNA editing value×relative transcript level)/100

The biomarker diagnostic performance could be characterized by: sensitivity, which represents its ability to detect the 'suicide attempters' group and specificity which represents its ability to detect the 'affective control' group. The results of the evaluation of a diagnostic test can be summarized in a 2×2 contingency table comparing these two well-defined groups. By fixing a cut-off, the two groups could be classified into categories according to the results of the test, categorized as either positive or negative. Given a particular biomarker, we can identify a number of a patients with a positive test result among the suicide attempters group (the "True Positive": TP) and b patients with a negative test result among the 'affective control' group (the "True Negative": TN). In the same fashion, c patients with a negative test result among the 'suicide attempters' group (the "False Negative": FN) and d patients with a positive test result among the 'affective control' group (the "False Positive": FP) are observed. Sensitivity is defined as TP/(TP+FN); which is herein referred to as the "true positive rate". Specificity is defined as TN/(TN+FP); which is herein referred to as the "true negative rate".

The accuracy of each biomarkers and its discriminatory power was evaluated using a Receiving Operating Characteristics (ROC) analysis. ROC curves are the graphical visualization of the reciprocal relation between the sensitivity (Se) and the specificity (Sp) of a test for various values.

In addition, all biomarkers were combined with each other to evaluate the potential increase in sensibility and specificity using a multivariate approaches as for example mROC program or logistic regression [14]. mROC is a dedicated program to identify the linear combination [15, 16], which maximizes the AUC (Area Under the Curve) ROC [17]. The equation for the respective combination is provided and can be used as a new virtual marker Z, as follows:

$Z = a \times \text{biomarker1} + b \times \text{biomarker2} + c \times \text{biomarker3}$, where a, b, c are calculated coefficients and biomarkers 1, 2, 3 are the level of biomarker.

Logistic regression model is applied to estimate the relative mood disorder risk using different combination of editing site(s) and/or isoforms and/or ADARs gene expression values for a patient.

A K-medians or K-means approach [18] was used to identify clusters of patients from the Interferon study. As example, the K-medians analysis was computed with the MEV v4.9 software (http://www.tm4.org/mev/) and Pearson or Euclidean correlation for distance. So, all patients present in the same cluster were considered different from patients of others clusters.

Example 2: Suicide Attempters Study

Characteristics of patients included in the clinical study are shown in Table I. This prospective study enrolled 38 patients that were all diagnosed with a psychiatric disorder: a group of 18 patients who never attempted suicide (affective controls, AC) compared to a group of 20 patients that all attempted suicide at least once (SA). Patient age ranged from 20 to 77 years old (mean±SD: 50.16±13.5). The cohort was constituted by 9 males (23.68%) and 29 females (76.32%). All the patients presented depressive disorders. Suicide attempt number ranged from 1 to 20 attempts, with a mean±SD of 3.4±4.52.

Example 3: Analysis of PDE8a mRNA Editing Using Next Generation Sequencing (NGS) Method We previously described a method used to determine the editing profile of the PDE8A mRNA using the capillary electrophoresis single-strand conformation polymorphism (CE-SSCP) technique (Patent PCT/EP2011/060444 filed on Jun. 24, 2011). Here, we developed a new experimental system for quantifying PDE8A RNA editing levels based on next-generation sequencing (NGS) which provides sufficient per-base depth to allow reliable quantification for all sites studied. Since this methodology is PCR based, we, first, selected several primer pairs to amplify the PDE8A mRNA region of interest (Table II). Different primer combinations meeting the following selection criteria to specifically amplify the region were tested: 1) the oligo's should be between 18-27 nucleotides long, 2) with preferentially a melting temperature surrounding 60° C. (57-63° C.), 3) an optimal GC content surrounding 50%, 4) a maximum allowable length of 5 mononucleotide repeat and 5) specifically amplify the region of interest depicted in FIG. 1. Since some primer pairs generated nonspecific amplification products that would interfere with accurate quantification of RNA editing an optimized primer pair is given comprising Seq2-Forward and Seq-3 Reverse (see Table II).

Example 4: Identification of New Editing Sites in Intron 9 of the PDE8a Human Gene by Ultra-Deep Sequencing Orlowski and collaborators have previously identified eight editing sites (A to H) in intron 9 of the PDE8A human gene (see Table III) [10]. Later, we identified six additional editing sites (I to N) in this same region (Patent PCT/EP2011/060444 filed on Jun. 24, 2011). Several studies pointed out that most ADAR activity takes place in clusters [19,20]. Not surprisingly, using NGS-based sequencing on SH-SY5Y human neuroblastoma cell line, we confirmed previously identified editing sites and identified new A- to I-editing sites in intron 9 of the PDE8A human gene. These new edited sites were called O, P, Q, R, S, T, U, V, W, X, Y, Z and ZZ (see Table III, FIG. 1). The presence of most of these editing sites (A to H, J to M, O, P, R to U and X to ZZ) were also identified in blood samples of some patients from the study with depressive patients and suicide attempters.

TABLE III

Listing of previously and newly identified A- to-I RNA editing sites in intron 9 of the PDE8A gene. For practical reason, optimization of the standard conditions for deep sequencing of the locus of interest within the PDE8A transcript was performed on human samples obtained from SH-SY5Y neuroblastoma cell-line. This allowed identification of yet unreported new editing sites in intron 9 of the PDE8A human gene (underlined in bold, Number 15 to 27). The new editing sites are named: O, P, Q, R, S, T, U, V, W, X, Y, Z and ZZ. Genomic coordinates are relative to the PDE8A on chromosome 15 for the human genome (GRCh38: 84,980,440). SH-SY5Y cell-line column refers to the editing sites identified in that particular human neuroblastoma cell line. Blood column refers to white blood cells collected on PAXgene Blood RNA tubes. X indicates when the editing site is measured at least in one patient with a cutoff > 0.1%.

| NB | Editing sites | Coordinates in PDE8A gene (GRCh38) | SH-SY5Y cell line | Blood |
|---|---|---|---|---|
| 1 | A | 85 096 686 | x | x |
| 2 | B | 85 096 687 | x | x |
| 3 | C | 85 096 717 | x | x |
| 4 | D | 85 096 719 | x | x |
| 5 | E | 85 096 720 | x | x |
| 6 | F | 85 096 729 | x | x |
| 7 | G | 85 096 798 | x | x |
| 8 | H | 85 096 649 | x | x |
| 9 | I | 85 096 663 | x | |
| 10 | J | 85 096 681 | x | x |
| 11 | K | 85 096 684 | x | x |
| 12 | L | 85 096 725 | x | x |
| 13 | M | 85 096 753 | x | x |
| 14 | N | 85 096 771 | x | |
| 15 | O | 85 096 653 | x | x |
| 16 | P | 85 096 654 | x | x |
| 17 | Q | 85 096 706 | x | |
| 18 | R | 85 096 728 | x | x |
| 19 | S | 85 096 735 | x | x |
| 20 | T | 85 096 737 | x | x |
| 21 | U | 85 096 748 | x | x |
| 22 | V | 85 096 759 | x | |
| 23 | W | 85 096 763 | x | |
| 24 | X | 85 096 764 | x | x |
| 25 | Y | 85 096 767 | x | x |
| 26 | Z | 85 096 796 | x | x |
| 27 | ZZ | 85 096 800 | x | x |

Figure 3:
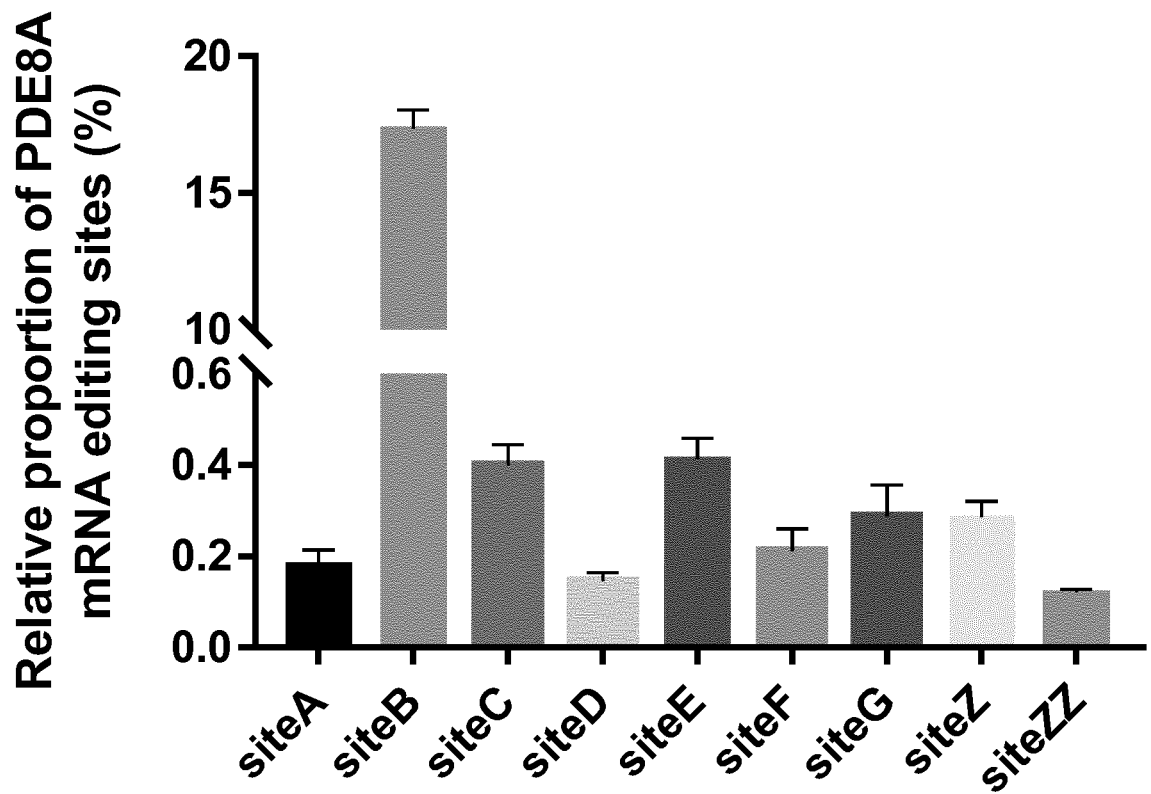
FIG. 3:
RNA editing sites identified in human white blood cells by ultra-deep sequencing. Figure reporting the relative proportion (mean±SEM) of RNA editing measured on several sites (A to G, Z and ZZ) of the PDE8A gene on the affective controls group.

Example 5: RNA Editing Sites Identified in Human White Blood Cells by Ultra-Deep Sequencing On table IV and FIG. 3 are reported only the RNA editing sites measured with a cutoff >0.1% from the affective controls group (mean±SEM). (See Table IV and FIG. 3).

TABLE IV

Table reporting the relative proportion (mean ± SEM) of RNA editing measured on several sites (A to G, Z and ZZ) of the PDE8A gene on the affective controls group. By definition the relative proportion of RNA editing at a given editing 'site' represents the sum of editing modifications measured at this unique genomic coordinate. Oppositely a mRNA isoform is a unique molecule that may or may not contain multiple editing modifications on the same transcript. Example given, PDE8A mRNA isoform BC contains a modification on both site B and site C within the same transcript.

| | Coordinates in PDE8A gene (GRCh38) | Relative proportion of editing (mean ± SEM) Affective controls (AC) |
|---|---|---|
| siteA | 85 096 686 | 0.18 ± 0.03 |
| siteB | 85 096 687 | 17.37 ± 0.66 |
| siteC | 85 096 717 | 0.40 ± 0.05 |
| siteD | 85 096 719 | 0.15 ± 0.02 |
| siteE | 85 096 720 | 0.41 ± 0.04 |
| siteF | 85 096 729 | 0.21 ± 0.05 |
| siteG | 85 096 798 | 0.29 ± 0.07 |

TABLE IV-continued

Table reporting the relative proportion (mean ± SEM) of RNA editing measured on several sites (A to G, Z and ZZ) of the PDE8A gene on the affective controls group. By definition the relative proportion of RNA editing at a given editing 'site' represents the sum of editing modifications measured at this unique genomic coordinate. Oppositely a mRNA isoform is a unique molecule that may or may not contain multiple editing modifications on the same transcript. Example given, PDE8A mRNA isoform BC contains a modification on both site B and site C within the same transcript.

|  | Coordinates in PDE8A gene (GRCh38) | Relative proportion of editing (mean ± SEM) Affective controls (AC) |
|---|---|---|
| siteZ | 85 096 796 | 0.28 ± 0.03 |
| siteZZ | 85 096 800 | 0.12 ± 0.01 |

Figures 4A, 4B, 4C, 4D:
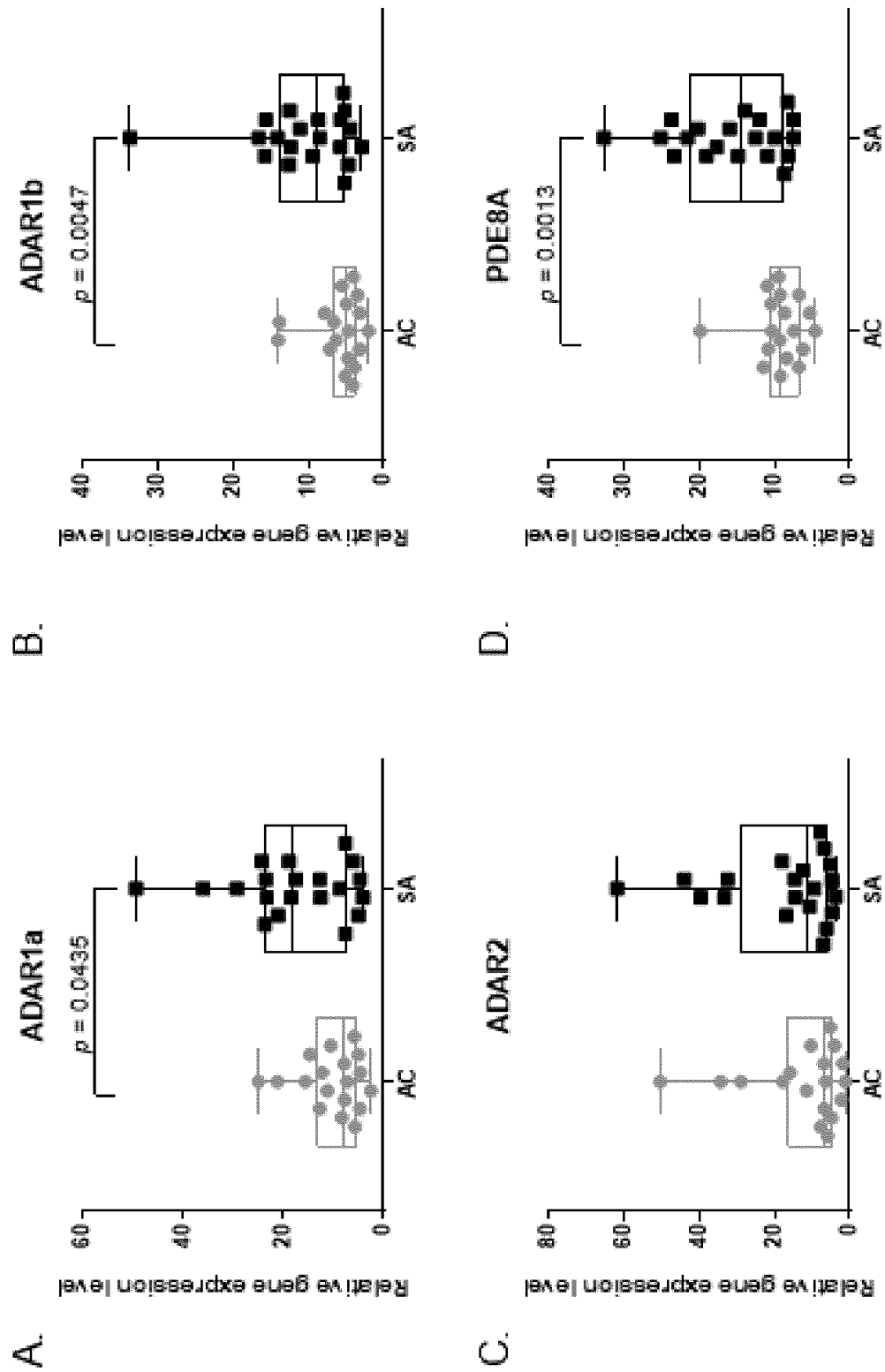
FIGS. 4A-4D: Expression levels of relevant genes measured by qPCR analysis in white blood cells in affective controls (AC) and suicide attempters (SA) populations. ADAR1a (A), ADAR1b (B), ADAR2 (C) and PDE8A (D) mRNA expression levels in affective controls (AC) compared to suicide attempters (SA). ADAR1a, ADAR1b, ADAR2 and PDE8A mRNA expression levels have been quantified in 38 patients (n=18 affective controls and n=20 suicide attempters). The expressions of the different transcripts were normalized to GAPDH and β2M gene expression. Measures were performed in triplicates. ADAR1a, 1b and PDE8A mRNA expression are significantly higher in suicide attempters. p-values were calculated using the Mann-Whitney test.

Example 6: Adar1a, 1B and 2 mRNA Expression are Increased in Suicide-Attempters 'Blood Using TaqMan® real-Time PCR assay, we analyzed ADAR1a, ADAR1b and ADAR2 mRNA gene expression by the so-called delta delta CT method (FIGS. 4A, 4B and 4C, respectively). ADAR1a, ADAR1b and ADAR2 expression levels varied from 2.6 to 25 (mean±SD: 10.2±6); 2.04 to 14.09 (mean±SD: 5.9±3.3) and 1.25 to 50.5 (mean±SD: 12.4±13.1), respectively in AC. In SA (n=20), ADAR1a, 1b and ADAR2 mRNA expression levels were comprised between 4.2 and 49.5 (mean±SD: 17.8±11.7); 3 and 33.8 (mean±SD: 10.6±7) and, 3.8 and 62 (mean±SD: 17.8±16.1), respectively. The expression of ADAR1a and ADAR1b genes were significantly higher in SA, mean 17.8 and 10.6, compared to AC: 10.2 and 5.9, respectively (p=0.0435 and 0.0047).

Example 7: Pde8a mRNA Expression is Higher in Suicide-Attempters

Likewise, an alteration of PDE8A expression level was observed in the SA group compared to the AC one (FIG. 4D). Indeed, PDE8A expression varied from 4.7 to 19.9 (mean±SD: 9.2±3.3), in AC, whereas its level ranged between 7.5 and 32.8 (mean±SD: 15.7±7.1) in SA. As well as for ADARs, PDE8A expression was significantly higher in the SA group than in the affective disorder one (p=0.0013) (FIG. 4D). This suggests that PDE8A could also provide an additional biomarker for suicide behavior.

Figure 5A:
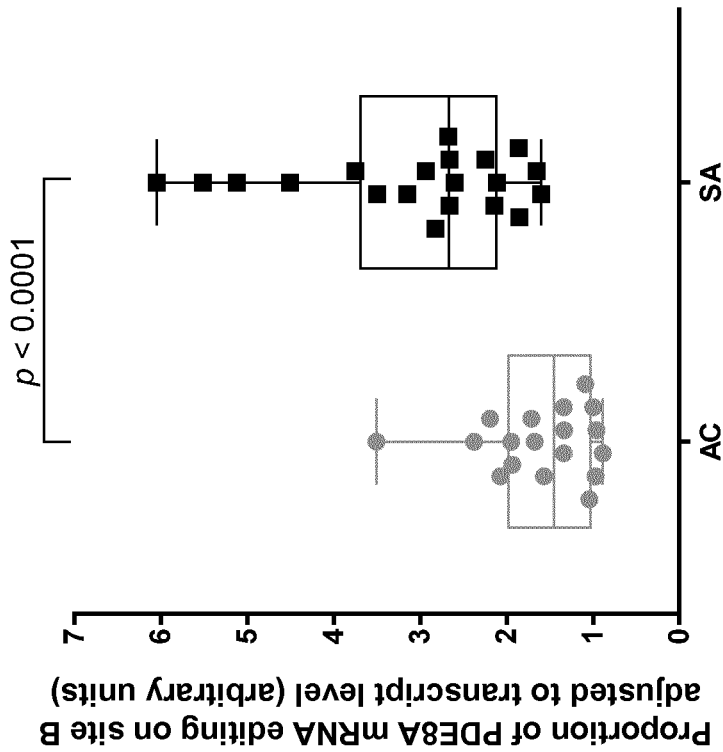
FIGS. 5A-5B: Relative proportion of RNA editing of the B site of PDE8A gene. (A) Boxplot of PDE8A B site mRNA editing is measured in affective controls (AC) and suicide attempters (SA). (B) PDE8A mRNA editing measurement adjusted to the relative transcript level. Data represent the mean of five independent experiments. The p-values were calculated using the Mann-Whitney test.
Figure 5B:
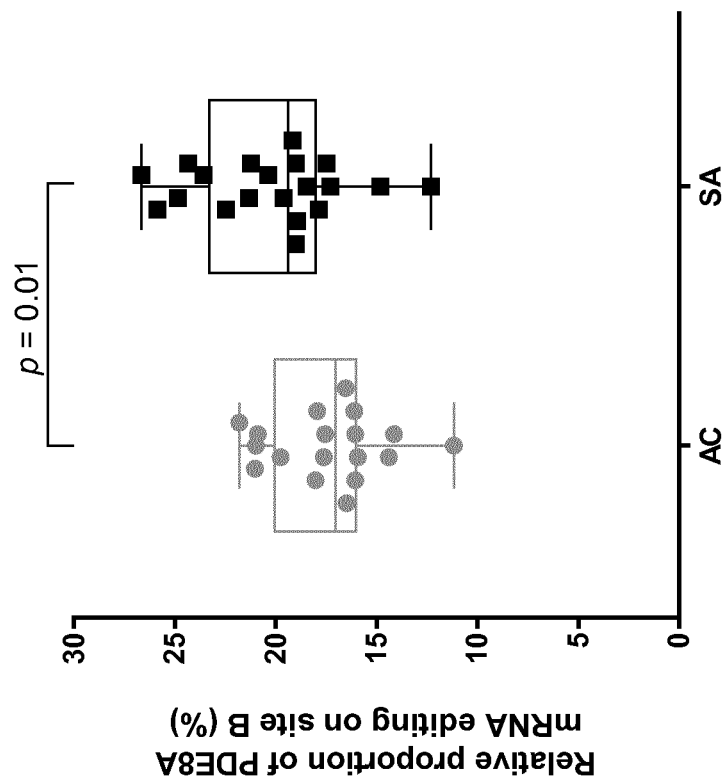

Example 8: Pde8a Site B mRNA Editing is Increased in Suicide-Attempters and Non-Edited (Ne) Pde8a Transcript is Decreased in Suicide-Attempters A) PDE8A Site B mRNA Editing Using NGS assay, we analyzed PDE8A mRNA editing profile in AC versus SA patients. As shown in FIG. 5A, we found that the relative proportion of the edited PDE8A mRNA B site is higher in SA compared to AC. In the AC (n=18), PDE8A edited transcripts were in a range of 11.2-21.8%, with a mean value of 17.4% (SD±2.8%). In the SA (n=20), the level of edited variants was in a range of 12.3-26.7%, with a mean value of 20.2% (SD±3.7%). The values for AC versus SA were significantly different (p=0.01). Further, we adjusted the relative proportion of RNA editing on the B site of PDE8A gene to the relative expression level of PDE8A mRNA (site B*). Results are presented in FIG. 5B. Adjusting the RNA editing on site B further enhanced differences between the AC and SA group as illustrated by the p-value (p<0.0001).

B) Non-Edited PDE8A Transcript

We analysed the relative proportion of the Non-edited PDE8A transcript in affective controls (AC) and suicide attempters (SA). The relative proportion of the Non-edited PDE8A transcript is higher in AC compared to SA. In the AC, the relative proportion of PDE8A Non-edited transcripts was in a range of 77.1-87.9%, with a mean value of 81.7% (SD±2.9%). In the SA, the level of the Non-edited transcript was in a range of 71.5-87.2%, with a mean value of 78.9% (SD±3.8%). The values for AC versus SA were significantly different (p=0.0094).

Example 9: Adjusted Pde8a mRNA Editing Along with Adar1a and Adar2 mRNA Expression as Blood Biomarkers for Suicidality We evaluated the diagnostic performance using the expression of ADARs and PDE8A (see Table V(A)), adjusted PDE8A mRNA editing on different sites (site A* to G*, Z* and ZZ*, table V(B)) and on different isoforms (Table V(C)) as biomarkers for suicidality using the receiver-operating characteristic (ROC) curve. Table V shows the results for each individual biomarker. We found the greatest area under the curve (AUC) for PDE8A site B* mRNA editing with a value of 0.878 (Table VB). Same results were obtained using PDE8A mRNA isoform B (Table V(C)).

TABLE V(A)

| NB Markers | AUC ROC | CI 95% | Threshold | Accuracy (%) | Specificity (%) | Sensitivity (%) | pValue |
|---|---|---|---|---|---|---|---|
| 1 PDE8A | 0.797 | [0.651; 0.943] | 11.7695 | 79.0 | 94.4 | 65.0 | 0.002 |
| 2 ADAR1b | 0.764 | [0.608; 0.919] | 8.2096 | 73.7 | 88.9 | 60.0 | 0.006 |
| 3 ADAR1a | 0.692 | [0.518; 0.865] | 16.6209 | 71.1 | 88.9 | 55.0 | 0.045 |
| 4 ADAR2 | 0.633 | [0.452; 0.815] | 7.0199 | 63.2 | 55.6 | 70.0 | 0.165 |

TABLE V(B)

| NB Markers | AUC ROC | CI 95% | Threshold | Accuracy (%) | Specificity (%) | Sensitivity (%) | pValue |
|---|---|---|---|---|---|---|---|
| 1 siteB* | 0.878 | [0.767; 0.989] | 2.0938 | 81.6 | 83.3 | 80.0 | 0.00002 |
| 2 siteC* | 0.864 | [0.751; 0.977] | 0.0493 | 79.0 | 77.8 | 80.0 | 0.0001 |
| 3 siteE* | 0.842 | [0.716; 0.967] | 0.0554 | 79.0 | 88.9 | 70.0 | 0.0002 |
| 4 siteF* | 0.786 | [0.633; 0.940] | 0.013 | 79.0 | 61.1 | 95.0 | 0.002 |

TABLE V(B)-continued

| NB | Markers | AUC ROC | CI 95% | Threshold | Accuracy (%) | Specificity (%) | Sensitivity (%) | pValue |
|---|---|---|---|---|---|---|---|---|
| 5 | siteZZ* | 0.778 | [0.624; 0.932] | 0.0142 | 76.3 | 94.4 | 60.0 | 0.003 |
| 6 | siteZ* | 0.750 | [0.589; 0.911] | 0.0247 | 73.7 | 66.7 | 80.0 | 0.008 |
| 7 | siteD* | 0.736 | [0.574; 0.898] | 0.0133 | 73.7 | 55.6 | 90.0 | 0.012 |
| 8 | siteA* | 0.683 | [0.508; 0.858] | 0.0245 | 68.4 | 94.4 | 45.0 | 0.05 |
| 9 | siteG* | 0.675 | [0.493; 0.857] | 0.025 | 68.4 | 72.2 | 65.0 | 0.07 |

TABLE V(C)

| NB | Markers | AUC ROC | CI 95% | Threshold | Accuracy (%) | Specificity (%) | Sensitivity (%) | pValue |
|---|---|---|---|---|---|---|---|---|
| 1 | IsoformB* | 0.878 | [0.769; 0.987] | 2.0039 | 81.6 | 83.3 | 80.0 | 0.00002 |
| 2 | IsoformBC* | 0.844 | [0.702; 0.987] | 0.0196 | 86.8 | 94.4 | 80.0 | 0.0001 |
| 3 | IsoformD* | 0.811 | [0.672; 0.951] | 0.0034 | 79.0 | 61.1 | 95.0 | 0.0007 |
| 4 | IsoformE* | 0.772 | [0.618; 0.926] | 0.0247 | 73.7 | 88.9 | 60.0 | 0.004 |
| 5 | IsoformNe* | 0.764 | [0.607; 0.921] | 9.7646 | 76.3 | 94.4 | 60.0 | 0.005 |
| 6 | IsoformBE* | 0.753 | [0.594; 0.911] | 0.0151 | 73.7 | 72.2 | 75.0 | 0.007 |
| 7 | IsoformG* | 0.739 | [0.572; 0.906] | 0.0224 | 73.7 | 83.3 | 65.0 | 0.01 |
| 8 | IsoformBG* | 0.733 | [0.568; 0.899] | 0.005 | 76.3 | 72.2 | 80.0 | 0.01 |
| 9 | IsoformBF* | 0.717 | [0.535; 0.898] | 0.0047 | 76.3 | 83.3 | 70.0 | 0.02 |
| 10 | IsoformA* | 0.703 | [0.53; 0.875] | 0.0021 | 71.1 | 88.9 | 55.0 | 0.03 |
| 11 | IsoformZ* | 0.700 | [0.528; 0.872] | 0.0173 | 71.1 | 83.3 | 60.0 | 0.04 |
| 12 | IsoformC* | 0.678 | [0.502; 0.854] | 0.0282 | 68.4 | 88.9 | 50.0 | 0.06 |
| 13 | IsoformF* | 0.675 | [0.493; 0.857] | 0.0045 | 73.7 | 55.6 | 90.0 | 0.07 |
| 14 | IsoformBZ* | 0.667 | [0.491; 0.843] | 0.0071 | 68.4 | 77.8 | 60.0 | 0.08 |
| 15 | IsoformBD* | 0.661 | [0.483; 0.839] | 0.0103 | 65.8 | 94.4 | 40.0 | 0.09 |

Tables V(A)-V(C): Diagnostic performances of the relative expression of ADARs and of PDE8A individual editing site and isoform. The table V(A) represents the diagnostic performances of the relative expression of ADAR1a, ADAR1b, ADAR2 and PDE8A. The table V(B) represents the diagnostic performances of individual editing site of PDE8A. The table V(C) represents the diagnostic performances of individual editing isoform of PDE8A or the non-edited transcript (Ne). Only the most relevant editing isoforms and editing sites defined as having a p-value<0.1 are presented, p-values were calculated using the Mann-Whitney test. The symbol * indicate that PDE8A editing site or editing isoforms are adjusted to its mRNA relative expression.

We further examined whether a combinatorial approach including PDE8A mRNA editing along with other biomarkers such as other PDE8A mRNA editing sites or isoforms and ADARs mRNA expression could enhance our ability to predict future suicide.

Figure 6:
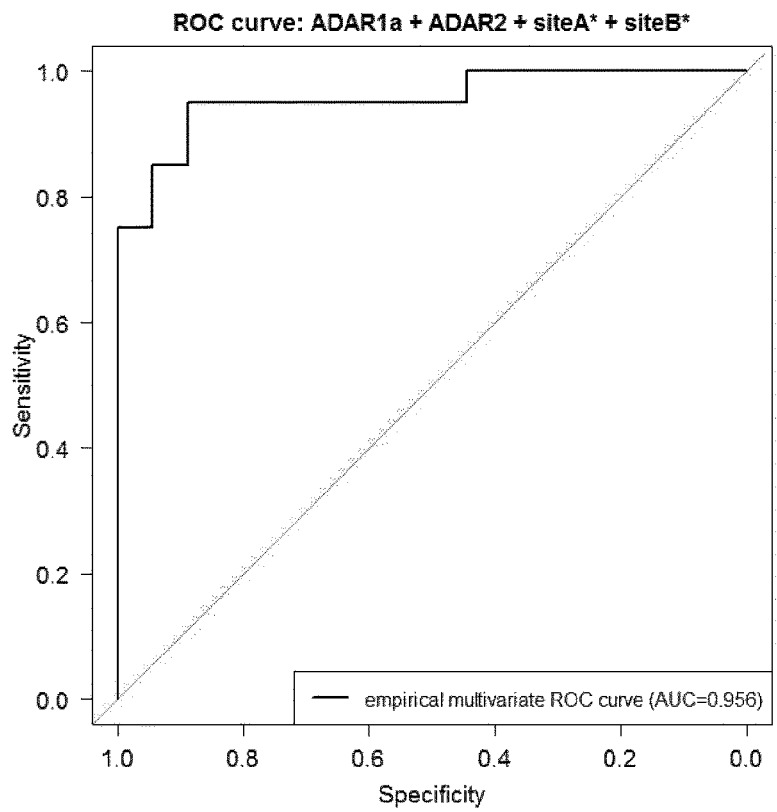
FIG. 6: Diagnostic performances of a combination of biomarkers using mROC approach. The figure illustrates an example of a multivariate ROC curve comparing affective controls to suicide attempters. ROC curve obtained with ADAR1a+ADAR2+PDE8A_siteA*+PDE8A_siteB* mROC combination.

For example, we found that the mROC curve improved from an AUC of 0.878 with PDE8A site B* editing alone, to an AUC of 0.956 by adding PDE8A site A* mRNA editing along with ADAR1a and ADAR2 mRNA expression (see Table VI and VII, lane 6 and FIG. 6). However, other combinations listed in Table VII gave good diagnostic performances with AUC between 0.878 (ADAR1b mRNA expression and PDE8A site B*, lane 30) and 0.964 (ADAR1a and ADAR2 mRNA and PDE8A isoform B, isoform BC and isoform D mRNA editing, lane 1).

TABLE VI

Table VI: Diagnostic performances of a combination of biomarkers. Table of associated diagnostic performances of a multivariate ROC curve comparing affective controls to suicide attempters and obtained with ADAR1a + ADAR2 + PDE8A_siteA* + PDE8A_siteB* combination.

| | Performances |
|---|---|
| Sensitivity % | 95.0 |
| Specificity % | 88.9 |
| Accuracy % | 92.1 |
| AUC ROC | 0.956 |
| Threshold (Z) | 1.6259 |

Figure 7:
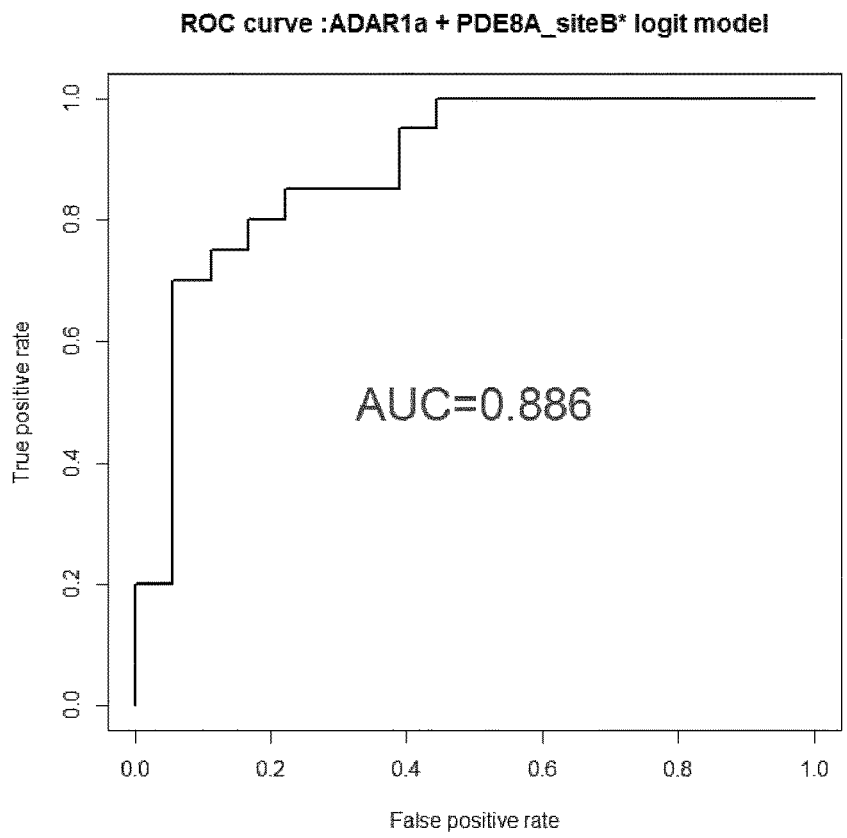
FIG. 7: Diagnostic performances of a combination of biomarkers using logistic regression. The figure illustrates an example of a multivariate ROC curve comparing affective controls to suicide attempters. ROC curve obtained with ADAR1a+PDE8A_siteB* logistic regression model.

Statistical analysis using logistic regression model or mROC approach yielded similar results (Table VIII, FIG. 7). Both methods showed an identical accuracy for ADAR1a mRNA expression+PDE8A siteB* mRNA editing (Table VII, lane29 and Table VIII, lane3 and/or FIG. 7).

TABLE VII

Table VII: Examples of diagnostic performances of biomarkers combinations. All combinations of biomarkers were performed by mROC approach. Combinations could be for example, association of ADARs mRNA expression and PDE8A RNA sites editing (adjusted* or not), association of ADARs mRNA expression and PDE8A RNA isoforms editing (adjusted* or not), association of PDE8A RNA sites editing (adjusted* or not), association of PDE8A RNA isoforms editing (adjusted* or not). As example, the equations for the biomarker combinations of ADAR1a + ADAR2 + PDE8A_siteA* + PDE8A_siteB* calculated by the mROC program could be: a) Z = 0.02327x[ADAR1a] − 0.026474x[ADAR2] − 16.6903xPDE8A_siteA* + 0.99311x[PDE8A_siteB*]. Using these equations a new virtual marker (Z) was calculated to perform the diagnostic of patient. The symbol * indicate that PDE8A editing site or editing isoforms are adjusted to its mRNA relative expression

| NB | Example of mROC Combinations | AUC ROC | CI 95% | Threshold | Accuracy (%) | Specificity (%) | Sensitivity (%) |
|---|---|---|---|---|---|---|---|
| 1 | ADAR1a + ADAR2 + PDE8A_IsoformB* + PDE8A_IsoformBC* + PDE8A_IsoformD* | 0.964 | [0.914; 1.000] | 1.831 | 92.1 | 88.9 | 95.0 |

TABLE VII-continued

Table VII: Examples of diagnostic performances of biomarkers combinations. All combinations of biomarkers were performed by mROC approach. Combinations could be for example, association of ADARs mRNA expression and PDE8A RNA sites editing (adjusted* or not), association of ADARs mRNA expression and PDE8A RNA isoforms editing (adjusted* or not), association of PDE8A RNA sites editing (adjusted* or not), association of PDE8A RNA isoforms editing (adjusted* or not). As example, the equations for the biomarker combinations of ADAR1a + ADAR2 + PDE8A_siteA* + PDE8A_siteB* calculated by the mROC program could be: a) Z = 0.02327x[ADAR1a] − 0.026474x[ADAR2] − 16.6903xPDE8A_siteA* + 0.99311x[PDE8A_siteB*]. Using these equations a new virtual marker (Z) was calculated to perform the diagnostic of patient. The symbol * indicate that PDE8A editing site or editing isoforms are adjusted to its mRNA relative expression

| NB | Example of mROC Combinations | AUC ROC | CI 95% | Threshold | Accuracy (%) | Specificity (%) | Sensitivity (%) |
|---|---|---|---|---|---|---|---|
| 2 | ADAR1a + ADAR2 + PDE8A_siteA* + PDE8A_siteB* + PDE8A_siteZZ* | 0.961 | [0.905; 1.000] | 1.641 | 92.1 | 88.9 | 95.0 |
| 3 | ADAR1a + ADAR2 + PDE8a + PDE8A_siteB + PDE8A_siteC | 0.961 | [0.909; 1.000] | 7.238 | 92.1 | 83.3 | 100.0 |
| 4 | ADAR2 + PDE8A_siteA* + PDE8A_siteB* + PDE8A_siteG* + PDE8A_siteZ* | 0.958 | [0.904; 1.000] | 1.677 | 92.1 | 94.4 | 90.0 |
| 5 | ADAR1a + ADAR1b + ADAR2 + PDE8A_IsoformB* + PDE8A_IsoformBF* | 0.958 | [0.900; 1.000] | 2.595 | 92.1 | 88.9 | 95.0 |
| 6 | ADAR1a + ADAR2 + PDE8A_siteA* + PDE8A_siteB* | 0.956 | [0.893; 1.000] | 1.626 | 92.1 | 88.9 | 95.0 |
| 7 | ADAR2 + PDE8a + PDE8A_IsoformB + PDE8A_IsoformBC | 0.953 | [0.894; 1.000] | 6.784 | 89.5 | 100.0 | 80.0 |
| 8 | ADAR2 + PDE8A_siteA* + PDE8A_siteB* | 0.950 | [0.890; 1.000] | 1.677 | 86.8 | 100.0 | 75.0 |
| 9 | ADAR1a + ADAR2 + PDE8A_IsoformB* + PDE8A_IsoformBF* | 0.950 | [0.886; 1.000] | 2.248 | 89.5 | 88.9 | 90.0 |
| 10 | ADAR1a + ADAR2 + PDE8a + PDE8A_siteA + PDE8A_siteB + PDE8A siteD | 0.950 | [0.887; 1.000] | 7.079 | 92.1 | 100.0 | 85.0 |
| 11 | ADAR1a + PDE8a + PDE8A_siteA + PDE8A_siteB + PDE8A_siteF + PDE8A_siteG | 0.950 | [0.881; 1.000] | 5.806 | 92.1 | 88.9 | 95.0 |
| 12 | ADAR1a + ADAR2 + PDE8A_siteA* + PDE8A_siteB* + PDE8A_siteD* | 0.942 | [0.871; 1.000] | 1.810 | 92.1 | 94.4 | 90.0 |
| 13 | ADAR1a + ADAR1b + PDE8A_siteA* + PDE8A_siteB* + PDE8A_siteG* | 0.933 | [0.847; 1.000] | 2.360 | 92.1 | 100.0 | 85.0 |
| 14 | ADAR1a + PDE8A_IsoformA* + PDE8A_IsoformB* + PDE8A_IsoformBC* + PDE8A_IsoformD* | 0.933 | [0.858; 1.000] | 2.264 | 89.5 | 100.0 | 80.0 |
| 15 | ADAR1a + PDE8a + PDE8A_siteB + PDE8A_siteF | 0.931 | [0.849; 1.000] | 5.888 | 89.5 | 83.3 | 95.0 |
| 16 | ADAR1a + PDE8A_siteA* + PDE8A_siteB* | 0.928 | [0.843; 1.000] | 1.617 | 86.8 | 94.4 | 80.0 |
| 17 | PDE8A_siteA* + PDE8A_siteB* + PDE8A_siteD* + PDE8A_siteF* + PDE8A_siteZ* | 0.925 | [0.843; 1.000] | 1.351 | 89.5 | 83.3 | 95.0 |
| 18 | PDE8A_IsoformA* + PDE8A_IsoformB* + PDE8A_IsoformBC* + PDE8A_IsoformBD* + PDE8A_IsoformD* | 0.925 | [0.840; 1.000] | 2.141 | 89.5 | 100.0 | 80.0 |
| 19 | PDE8A_siteA* + PDE8A_siteB* + PDE8A_siteD* + PDE8A_siteE* + PDE8A_siteF* | 0.922 | [0.838; 1.000] | 1.335 | 89.5 | 83.3 | 95.0 |
| 20 | ADAR1a + ADAR1b + ADAR2 + PDE8A_siteB* | 0.919 | [0.831; 1.000] | 1.935 | 86.8 | 77.8 | 95.0 |
| 21 | PDE8a + PDE8A siteB + PDE8A_siteC | 0.919 | [0.834; 1.000] | 6.212 | 89.5 | 83.3 | 95.0 |
| 22 | ADAR1b + PDE8A_siteA* + PDE8A_siteB* + PDE8A_siteD* | 0.917 | [0.828; 1.000] | 1.361 | 89.5 | 83.3 | 95.0 |
| 23 | PDE8A_siteA* + PDE8A_siteB* + PDE8A_siteD* | 0.917 | [0.828; 1.000] | 1.357 | 89.5 | 83.3 | 95.0 |
| 24 | ADAR1a + ADAR1b + PDE8A_siteB* + PDE8A_siteD* | 0.914 | [0.820; 1.000] | 2.105 | 89.5 | 94.4 | 85.0 |
| 25 | ADAR1a + ADAR1b + ADAR2 + PDE8A_IsoformB* | 0.911 | [0.818; 1.000] | 1.948 | 86.8 | 77.8 | 95.0 |
| 26 | ADAR1a + ADAR1b + PDE8A_siteB* | 0.908 | [0.812; 1.000] | 2.196 | 86.8 | 94.4 | 80.0 |
| 27 | PDE8A_siteA* + PDE8A_siteB* | 0.908 | [0.816; 1.000] | 1.356 | 86.8 | 88.9 | 85.0 |
| 28 | ADAR2 + PDE8A_siteB* | 0.906 | [0.809; 1.000] | 1.541 | 86.8 | 83.3 | 90.0 |
| 29 | ADAR1a + PDE8A_siteB* | 0.886 | [0.776; 0.996] | 1.750 | 81.6 | 94.4 | 70.0 |
| 30 | ADAR1b + PDE8A_siteB* | 0.878 | [0.767; 0.989] | 1.451 | 81.6 | 83.3 | 80.0 |

TABLE VIII

Table VIII: Examples of diagnostic performances of biomarkers combination using logistic regression (AC versus SA). The accuracy of biomarkers combination and its discriminatory power were evaluated using a logistic regression. Combinations could be for example, association of ADARs expression and PDE8A RNA sites editing (adjusted* or not), association of ADARs mRNA expression and PDE8A RNA isoforms editing (adjusted* or not), association of PDE8A RNA sites editing (adjusted* or not), association of PDE8A RNA isoforms editing (adjusted* or not). As example, the equations for the biomarker combinations of ADAR1a + PDE8A_siteB* calculated by logistic regression could be: P = Logit-1(0.0564x[ADAR1a] + 1.9012x[PDE8A_siteB* − 4.68849], Using these equations a probability P was calculated to perform the diagnostic of patient. P(logit) is the probability for a patient to belong to the category "Suicide attempters". The symbol * indicate that PDE8A editing site or editing isoforms are adjusted to its mRNA relative expression.

| NB | Examples of multivariate logistic regression | AUC ROC | P(logit) | Accuracy (%) | Specificity (%) | Sensitivity (%) |
|---|---|---|---|---|---|---|
| 1 | PDE8A_siteA* + PDE8A_siteB* | 0.914 | 0.45 | 86.8 | 83.3 | 90.0 |
| 2 | PDE8A IsoformB* + PDE8A_IsoformBC* | 0.897 | 0.55 | 84.2 | 88.9 | 80.0 |
| 3 | ADAR1a + PDE8A_siteB* | 0.886 | 0.50 | 81.6 | 83.3 | 80.0 |
| 4 | ADAR1a + PDE8A_IsoformB* | 0.886 | 0.65 | 81.6 | 94.4 | 70.0 |

Figures 9A, 9B, 9C, 9D:
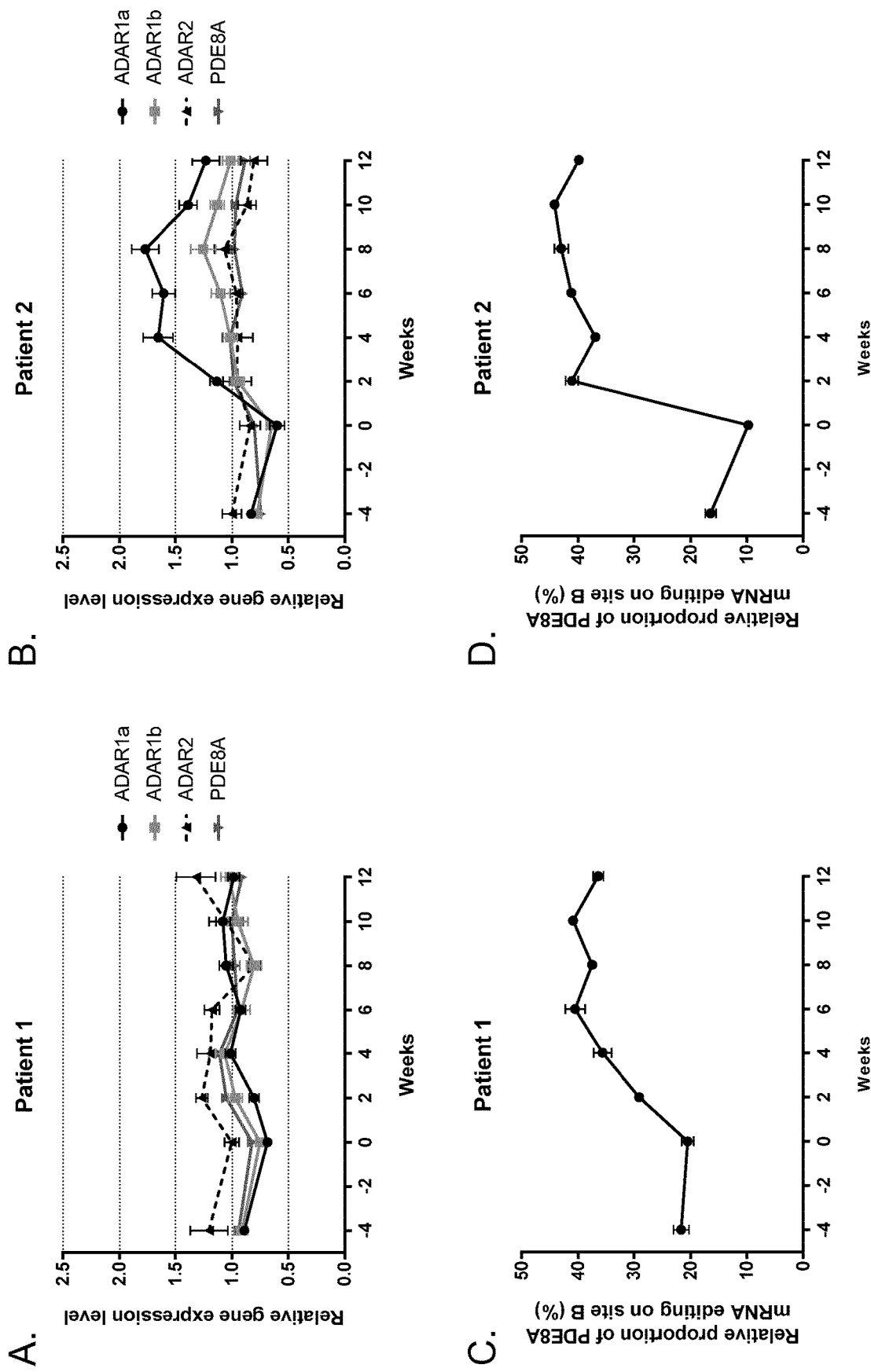
FIGS. 9A-9D: Longitudinal analysis of expression levels of relevant genes (A-B) and relative proportion of RNA editing (C-D) of the B site of PDE8A gene on 2 hepatitis C virus (HCV) infected patients treated with IFN-α and ribavirin. Data shown are means±SD (error bars) of five independent experiments (n=5) measured for each patient at each time-point.
Figure 10:
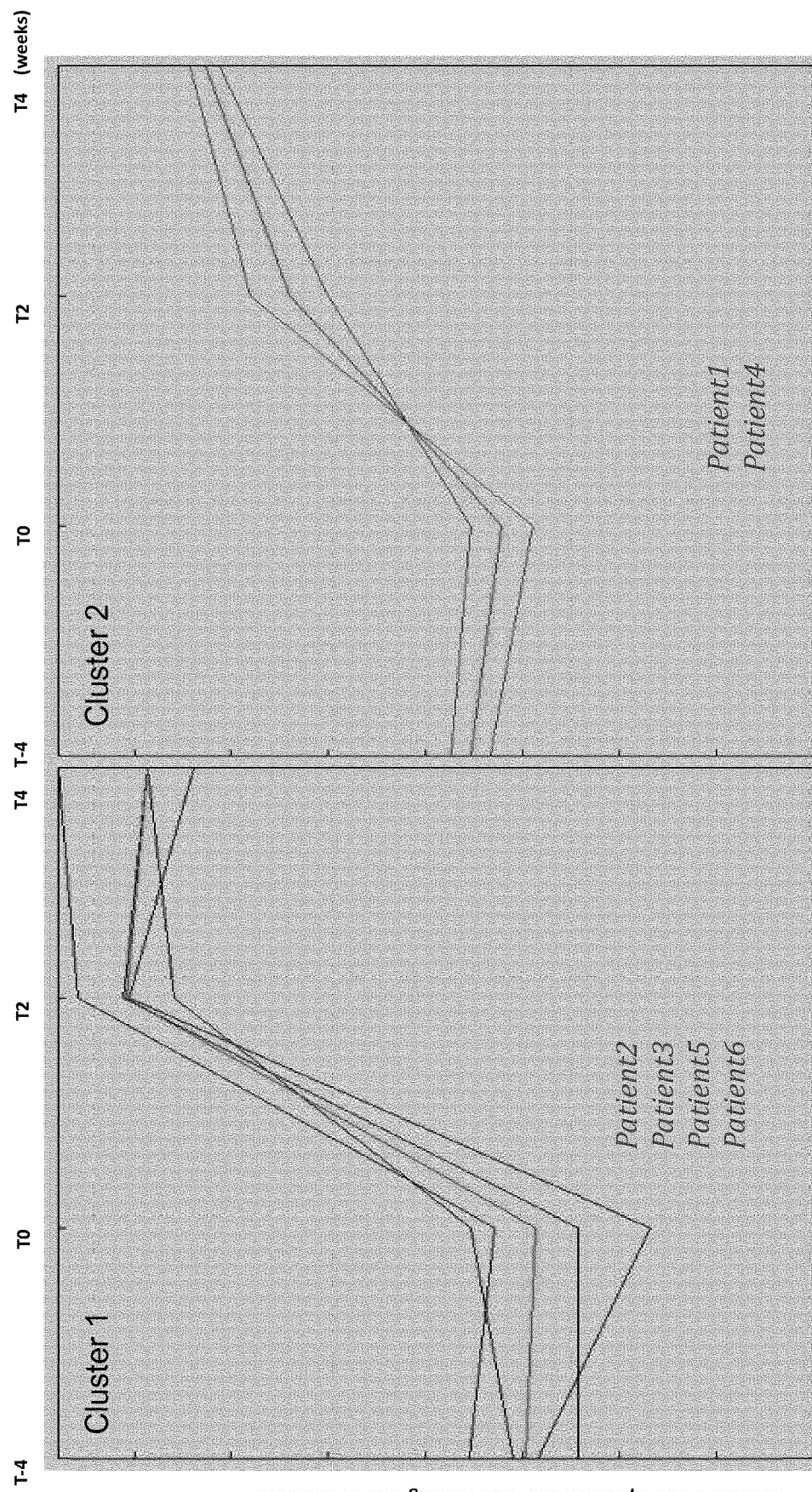
FIG. 10: Clustering analysis of six HCV infected patients included in the IFN study. K-Median cluster output using MEV software v4.9, with Pearson correlation for distance, 1000 iterations and 2 clusters are chosen as parameters. This approach resulted in 2 different clusters of patients. The first cluster including 4 patients displaying a rapid and strong response to IFN increase as observed by the steep slope of the curve over the initial 4 weeks of treatment. A second cluster gathering two patients with a blunted IFN response could also be observed.

Example 10: Increased PDE8a mRNA Editing in Hepatitis C Virus (HCV)-Infected Patients During IFN-α Therapy Major depression during IFN-α therapy for chronic hepatitis C virus (HCV) infection is common, with an incidence up to 45% [21]. This model represents a unique opportunity to assess individuals for depression and/or drug-induced psychiatric adverse effects within a short period of time (weeks). The longitudinal study has the major advantage that each patient acts as his own reference control ruling out genetic variability and environmental influence. In addition, ADAR1a is inducible by interferon stimulation [22]. In this study, we investigate whether PDE8A mRNA editing is modified during IFN-α treatment in HCV patients. 6 patients with HCV were assessed prospectively, 4 weeks before treatment, and every two weeks over 12-weeks of IFN-α and ribavirin treatment (FIG. 8). In a general manner, we observed that PDE8A mRNA editing on B site is increased in all patients after IFN-α treatment. As example, by further analyzing the relative proportion of the RNA editing on PDE8A individual sites and ADARs gene expression in two representative patients, we could observe clear differences in response to IFN-α treatment between individuals. In patient 1, no induction of ADARs gene expression could be observed and a blunted increase in PDE8A RNA editing in response to IFN-α response (FIG. 9A, 9C). Oppositely, in patient 2 a rapid and strong increase of ADARs expression could be observed (FIG. 9B) as well as a strong and rapid increase in PDE8A RNA editing (FIG. 9D). In a general manner, by using a k-medians approach, the clustering of all six patients confirmed the different IFN-α mediated response and suggested two separate groups of patients (FIG. 10). A first group of patients (cluster1) with a marked and rapid IFN-α mediated response on both ADAR1a transcript level and PDE8A editing on site B, as observed by the steep slope of the curves (FIG. 10). A second group of patients (cluster2) with a blunted response compared to the other patients, as observed for patient 1 (FIGS. 9A-9C). All patients have been clinically evaluated using MADRS (Montgomery and Asberg Depression Scale), MINI (Mini International Neuropsychiatric Interview), MAThyS (Multidimensional Assessment of Thymic States scale) and YMRS (Young Mania Rating Scale) tests. Psychiatric evaluation clearly showed modifications of the mood such as irritability and/or depressive states as measured by abovementioned tests.

Example 11: Decreased Pde8a mRNA Editing in Non-Repeat Suicide Attempters Over Time Suicide attempt constitutes one of the strongest risk factors for future attempts [23,24]. During one year after the suicide, the rate of suicide reattempts range from 12-15% [25, 26]. In a follow up study including 28 patients (table I(B), we analyzed the clinical evaluations of these patients at initial visit and 6 months later. We divided the whole group in 2 different subgroups; the first group (n=20) that did not reattempt suicide (NRSA) and the second group of patients (n=8) who have attempted suicide (RSA) at least once during the period. The average number of suicide attempts in this group during the 6 months follow-up period was 1.875. Three independent clinical evaluation scores (Hamilton, MADRS and BDI) were used to monitor the patients and the BDI score showed a significant improvement during follow up in the NRSA group (FIG. 11A). On the other hand, the clinical evaluations in the RSA group did not show improvement and even showed significant worsening of the MADRS score (FIG. 11B). To compare the clinical evaluations to the biomarkers (RNA editing of the PDE8A gene), we analyzed RNA editing in the white blood cells of these patients at the time of the follow up evaluation (FIGS. 11C and 11D). We investigated whether PDE8A mRNA editing is modulated between non-repeat suicide attempters (NRSA) and repeat suicide attempters (RSA) over a 6-month period. Interestingly, all PDE8A mRNA editing sites showed significant changes in the NRSA group whereas only B site was modified in the RSA group, suggestively signing improvement of the mental state of the patients.

Example 12: Modified PDE8a mRNA Editing in Hepatitis C Virus (HCV)-Infected Patients During IFN-α Therapy Major depression during IFN-α therapy for chronic hepatitis C virus (HCV) infection is common, with an incidence up to 45% [21]. This model represents a unique opportunity to assess individuals for depression and/or drug-induced psychiatric adverse effects within a short period of time (weeks). In this study, we took advantage of the well-documented and well-characterized mood alterations observed in hepatitis C infected patients undergoing antiviral therapy with IFN and Ribavirin. A small cohort of ten individuals with hepatitis C virus without prior records for psychiatric disorders was recruited over different medical hospitals in France. At inclusion, patients underwent harmonized psychiatric assessment and at repeated interval during the course of treatment. In this particular setting, every patient acts as its own control and evolution of the patient can be monitored over time. All patients have been clinically evaluated using MADRS (Montgomery and Asberg Depression Scale), MINI (Mini International Neuropsychiatric Interview), MAThyS (Multidimensional Assessment of Thymic States scale) and YMRS (Young Mania Rating Scale) tests. Psychiatric evaluation clearly showed modifications of the mood such as irritability and/or depressive states as measured by abovementioned tests. To further study in more detail the events occurring in each patient treated with IFN, we analyzed MADRS scores during the 12 weeks of the treatment. We considered every patient with a high MADRS score combined with emotional reactivity as undergoing a mood alteration (depression). Out of the 10 patients, three patients were classified as having a depressive episode.

Figure 13A:
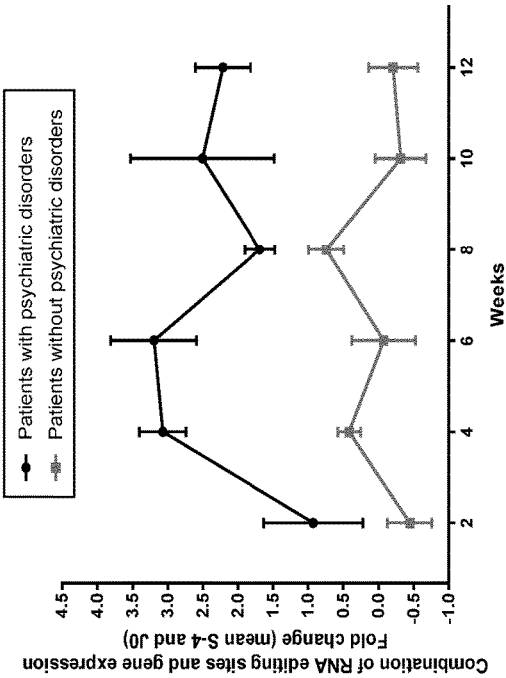
FIGS. 13A-13C: (A) Longitudinal analysis of a combination of biomarkers composed of ADAR gene expression in the group of patients with depressive episodes (n=3) and without (n=7). (B) Longitudinal analysis of a combination of biomarkers composed of RNA editing in the group of patients with depressive episodes (n=3) and without (n=7). (C) ROC curve of a combination of biomarkers to separate the population with and without depressive episodes.
Figure 13B:
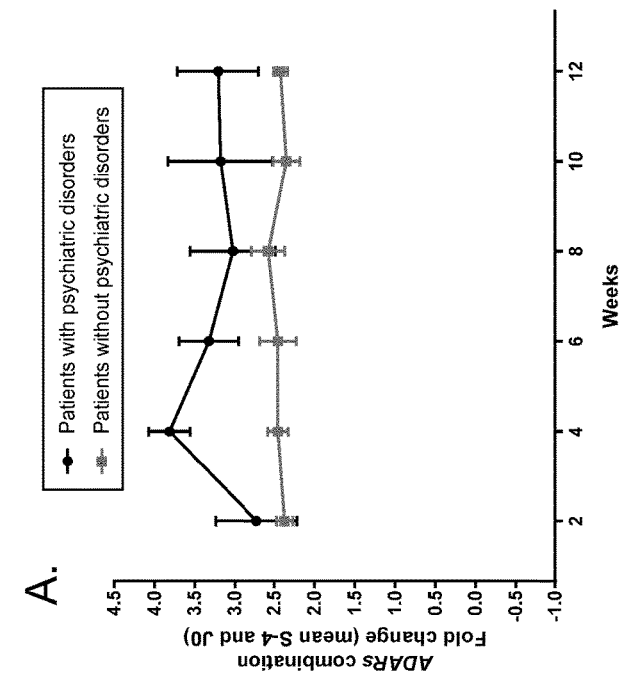
Figure 13C:
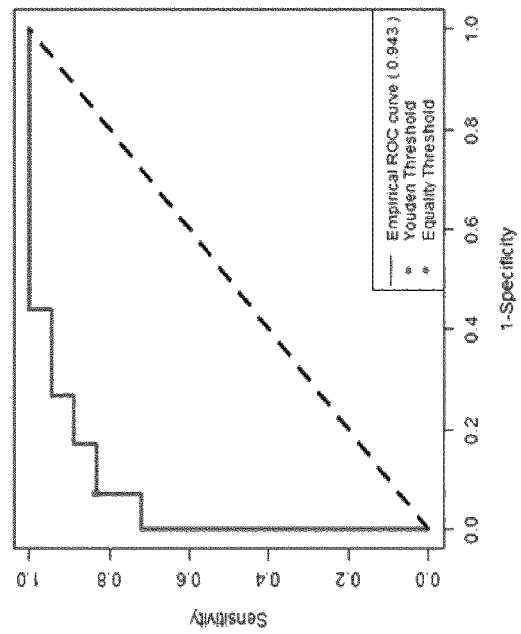

The longitudinal study has the major advantage that each patient acts as his own reference control ruling out genetic variability and environmental influence. In addition, ADAR1a is inducible by interferon stimulation [22]. While ADAR2 gene expression did not change during the course of the treatment, a clear upregulation of ADAR1a and ADAR1b transcript level was observed as early as two weeks after onset of therapy (FIG. 12A, Table IX)). The similar expression profile that was observed between ADAR1a, ADAR1b, and PDE8A suggest that these genes are altered specifically by antiviral treatment. By applying the ultra-deep sequencing approach the RNA editing of the PDE8A gene adjusted to the relative PDE8A transcript level was analyzed and computed (FIG. 12B). Since PDE8A gene expression significantly increased during course of the treatment, RNA editing of the PDE8A gene analysis was performed by adjusting to the relative PDE8A transcript level. Remarkably, the RNA editing increase of the PDE8A transcript was highly homogenous over the whole studied population and overall editing on the B site of the PDE8A transcript doubled within two weeks. The overall increase of RNA editing on these sites reached a plateau level between 2 and 4 weeks after therapy onset (FIG. 12C). Consistent with previous data obtained in SH-SY5Y, IFN injection in hepatitis C infected patients induced a rapid and strong increase in RNA editing activity in the white blood cells of the patients. By combining gene expression data a marked difference between group with and without depressive episodes was observed (FIG. 13A). Interestingly, a similar separation was also observed by specifically analyzing RNA editing of PDE8A transcript combined with gene expression data (FIG. 13B). Combining RNA editing and specific gene expression biomarkers showed high specificity and sensitivity in identifying IFN treated patients at risk to experience a psychiatric event during the course of the treatment (Table X, FIG. 13D). Finally by applying identified algorithm to all patients at all time points, we tested the combined biomarkers to identify at risk patients (FIG. 14). The combination of biomarkers was highly robust over the whole course of the pilot study to detect the three patients that developed a depression, 3 out of 18 (16%) calls were false negatives. On the other hand only 3 out the 42 results in the group of patients that did not show clinical signs of depression were false positives (7%). Overall, identified blood biomarkers allow accurate and robust detection of patients that are at risk to develop a depression in the context of a pharmacological treatment such as IFN.

TABLE IX

TABLE IX: Statistics of the gene expression data prior and after onset of antiviral therapy. The Table IX recapitulates the p-values as obtained by Wilcoxon testing, fold induction and Area under the ROC curve (AUC). As ADAR1a, ADAR1b and PDE8A significantly increased, ADAR2 expression did not vary during the course of the study.

|        | pWILCOXON | foldchange | AUC   |
|--------|-----------|------------|-------|
| ADAR1a | 2.76E−07  | 1.57       | 0.897 |
| ADAR1b | 8.83E−08  | 1.33       | 0.914 |
| PDE8A  | 5.42E−04  | 1.12       | 0.767 |
| ADARB1 | 0.82      | 1.01       | 0.518 |

TABLE X

TABLE X: Diagnostic performance: Specificity and sensitivity in identifying IFN treated patients at risk to experience a psychiatric event during the course of the treatment

| Accuracy    | 89.8% |
| Specificity | 92.7% |
| Sensitivity | 83.3% |
| PPV         | 83.3% |
| NPV         | 92.7% |

BIBLIOGRAPHY

1. Ernst C, Deleva V, Deng X, Sequeira A, Pomarenski A, et al. (2009) Alternative splicing, methylation state, and expression profile of tropomyosin-related kinase B in the frontal cortex of suicide completers. Arch Gen Psychiatry 66: 22-32.
2. Bani-Fatemi A, Howe A S, De Luca V (2015) Epigenetic studies of suicidal behavior. Neurocase 21: 134-143.
3. Kaminsky Z, Wilcox H C, Eaton W W, Van Eck K, Kilaru V, et al. (2015) Epigenetic and genetic variation at SKA2 predict suicidal behavior and post-traumatic stress disorder. Transl Psychiatry 5: e627.
4. Cavarec L, Vincent L, Le Borgne C, Plusquellec C, Ollivier N, et al. (2013) In vitro screening for drug-induced depression and/or suicidal adverse effects: a new toxicogenomic assay based on CE-SSCP analysis of HTR2C mRNA editing in SH-SY5Y cells. Neurotox Res 23: 49-62.
5. Karanovic J, Svikovic S, Pantovic M, Durica S, Brajuskovic G, et al. (2015) Joint effect of ADARB1 gene, HTR2C gene and stressful life events on suicide attempt risk in patients with major psychiatric disorders. World J Biol Psychiatry 16: 261-271.
6. Dracheva S, Patel N, Woo D A, Marcus S M, Siever L J, et al. (2008) Increased serotonin 2C receptor mRNA editing: a possible risk factor for suicide. Mol Psychiatry 13: 1001-1010.
7. Dracheva S, Chin B, Haroutunian V (2008) Altered serotonin 2C receptor RNA splicing in suicide: association with editing. Neuroreport 19: 379-382.
8. Simmons M, Meador-Woodruff J H, Sodhi M S (2010) Increased cortical expression of an RNA editing enzyme occurs in major depressive suicide victims. Neuroreport 21: 993-997.
9. Wang P, Wu P, Egan R W, Billah M M (2001) Human phosphodiesterase 8A splice variants: cloning, gene organization, and tissue distribution. Gene 280: 183-194.
10. Orlowski R J, O'Rourke K S, Olorenshaw I, Hawkins G A, Maas S, et al. (2008) Altered editing in cyclic nucleotide phosphodiesterase 8A1 gene transcripts of systemic lupus erythematosus T lymphocytes. Immunology 125: 408-419.
11. Morse D P, Aruscavage P J, Bass B L (2002) RNA hairpins in noncoding regions of human brain and *Caenorhabditis elegans* mRNA are edited by adenosine deaminases that act on RNA. Proc Natl Acad Sci USA 99: 7906-7911.
12. Youngchao Ge S D, Terence P. Speed (2003) Resampling-based multiple testing for microarray data analysis. Test 12: 1-77.
13. Gentleman R C, Carey V J, Bates D M, Bolstad B, Dettling M, et al. (2004) Bioconductor: open software development for computational biology and bioinformatics. Genome Biol 5: R80.
14. Kramar A F D, Fortuné A, Reiser B (2001) mROC: A computer program for combining tumour predicting disease states. Comput Methods Programs Biomed 66: 199-207.
15. Su J Q L J (1993) Linear combinations of multiple diagnostic markers. Journal of the American Statistical Association. Journal of the American Statistical Association: 1350-1355.
16. Wang H (2007) A note on iterative marginal optimization: a simple algorithm for maximum rank correlation estimation. Computational Statistics and Data Analysis 2803-2812.
17. Staack A, Badendieck S, Schnorr D, Loening S A, Jung K (2006) Combined determination of plasma MMP2, MMP9, and TIMP1 improves the non-invasive detection of transitional cell carcinoma of the bladder. BMC Urol 6: 19.
18. Soukas A, Cohen P, Socci N D, Friedman J M (2000) Leptin-specific patterns of gene expression in white adipose tissue. Genes Dev 14: 963-980.

19. Levanon E Y, Eisenberg E, Yelin R, Nemzer S, Hallegger M, et al. (2004) Systematic identification of abundant A-to-I editing sites in the human transcriptome. Nat Biotechnol 22: 1001-1005.
20. Porath H T, Carmi S, Levanon E Y (2014) A genome-wide map of hyper-edited RNA reveals numerous new sites. Nat Commun 5: 4726.21. Asnis G M, De La Garza R, 2nd (2006) Interferon-induced depression in chronic hepatitis C: a review of its prevalence, risk factors, biology, and treatment approaches. J Clin Gastroenterol 40: 322-335.
21. Asnis G M, De La Garza R, 2nd (2006) Interferon-induced depression in chronic hepatitis C: a review of its prevalence, risk factors, biology, and treatment approaches. J Clin Gastroenterol 40: 322-335.
22. George C X, Samuel C E (1999) Human RNA-specific adenosine deaminase ADAR1 transcripts possess alternative exon 1 structures that initiate from different promoters, one constitutively active and the other interferon inducible. Proc Natl Acad Sci USA 96: 4621-4626.
23. Borges G, Angst J, Nock M K, Ruscio A M, Walters E E, et al. (2006) A risk index for 12-month suicide attempts in the National Comorbidity Survey Replication (NCS-R). Psychol Med 36: 1747-1757.
24. Brown G K, Beck A T, Steer R A, Grisham J R (2000) Risk factors for suicide in psychiatric outpatients: a 20-year prospective study. J Consult Clin Psychol 68: 371-377.
25. Cedereke M, Ojehagen A (2005) Prediction of repeated parasuicide after 1-12 months. Eur Psychiatry 20: 101-109.
26. Heyerdahl F, Bjornaas M A, Dahl R, Hovda K E, Nore A K, et al. (2009) Repetition of acute poisoning in Oslo: 1-year prospective study. Br J Psychiatry 194: 73-79.

The invention claimed is:

1. An in vitro method for measuring alterations of A-to-I editing on PDE8A transcripts in a blood sample of a subject at risk for having depression, or having one or more clinical signs of depression, with or without the risk of suicide attempts, comprising:
(a) in a same cellular RNA extract obtained from the blood sample from the subject containing cells expressing PDE8A and at least one of the editing enzymes ADAR1a, ADAR1b and ADAR2, determining:
i) the PDE8A mRNA expression level, and
ii) the level of the PDE8A RNA A-to-I editing of at least one or a combination of sites that can be edited on the PDE8A gene) to give an RNA editing value; and
(b) determining the adjusted relative proportion of said RNA editing site(s) to the PDE8A mRNA expression level from the results obtained in step (a) as an adjusted editing value,
wherein the adjusted editing value=(RNA editing value× relative transcript level 100);
wherein the RNA editing value of a particular edit=100× the number of sites having that particular edit/the sum of all the edits in that site; and
wherein the relative transcript level represents the total RNA level of all transcripts for PDE8A relative to the RNA level of a housekeeping gene.

2. The method of claim 1, wherein in step (a), the determination of the PDE8A RNA editing value is done for at least one site selected from the group of edited sites consisting of sites A,B,C,D,E,F,G,H,I,J, K,L,M,N,O,P,Q,R, S,T,U,V,W,X,Y,Z and ZZ.

3. The method of claim 2, wherein at least one edited site is selected from the group of edited sites consisting of sites O,P,Q,R,S,T,U,V,W,X,Y,Z and ZZ.

4. The method of claim 1, further comprising determining the relative proportion of said PDE8A RNA editing site(s) from the results obtained in step (a) in combination with the mRNA expression levels of the enzymes ADAR1a, ADAR1b, and/or ADAR2.

5. The method of claim 1, wherein the determination of the PDE8A mRNA expression level is carried out by qPCR or by the NGS (Next Generation Sequencing).

6. The method of claim 1, wherein at least one edited site is site B.

7. The method of claim 1, wherein the determination of the level of RNA editing of PDE8A on at least one site is carried out by the set of primers selected from the group consisting of:
Seq1-Forward (SEQ ID No.2) or Seq2-Forward (SEQ ID No.3) for the forward primer; and/or
Seq1-Reverse (SEQ ID No.4), Seq2-Reverse (SEQ ID No.5) or Seq3-Reverse (SEQ ID No.6) for the reverse primer.

8. The method of claim 7, wherein the set of primers comprises Seq2-Forward (SEQ ID No.3) and Seq3-Reverse (SEQ ID No.6).

* * * * *